(12) United States Patent
Igawa et al.

(10) Patent No.: US 12,054,544 B2
(45) Date of Patent: Aug. 6, 2024

(54) COMPOSITIONS COMPRISING ANTIGEN-BINDING MOLECULES

(71) Applicant: Chugai Seiyaku Kabushiki Kaisha, Tokyo (JP)

(72) Inventors: Tomoyuki Igawa, Shizuoka (JP);
Hitoshi Katada, Shizuoka (JP);
Takeaki Kawai, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 303 days.

(21) Appl. No.: 16/488,115

(22) PCT Filed: Feb. 23, 2018

(86) PCT No.: PCT/JP2018/006626
§ 371 (c)(1),
(2) Date: Aug. 22, 2019

(87) PCT Pub. No.: WO2018/155611
PCT Pub. Date: Aug. 30, 2018

(65) Prior Publication Data
US 2019/0382484 A1    Dec. 19, 2019

(30) Foreign Application Priority Data
Feb. 24, 2017    (JP) ................................ 2017-033564

(51) Int. Cl.
*C07K 16/28*     (2006.01)
*A61K 39/00*     (2006.01)
*G01N 33/68*     (2006.01)

(52) U.S. Cl.
CPC ..... *C07K 16/2803* (2013.01); *G01N 33/6854* (2013.01); *A61K 2039/505* (2013.01); *C07K 2317/526* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2005/0136051 A1* | 6/2005 | Scallon ................. | C07K 16/36 424/133.1 |
| 2010/0015133 A1* | 1/2010 | Igawa ................... | C07K 16/18 536/23.53 |
| 2010/0105874 A1* | 4/2010 | Schuurman .......... | C07K 16/468 530/387.3 |
| 2012/0201746 A1* | 8/2012 | Liu ....................... | C07K 16/468 424/1.11 |
| 2013/0115208 A1* | 5/2013 | Ho ........................ | C07K 16/468 424/133.1 |
| 2013/0336981 A1* | 12/2013 | de Kruif ............... | A61K 39/40 424/136.1 |
| 2014/0079689 A1* | 3/2014 | Elliott .................. | C07K 16/247 424/133.1 |
| 2014/0154254 A1* | 6/2014 | Kannan ................ | C07K 16/468 435/254.2 |
| 2014/0199294 A1 | 7/2014 | Mimoto et al. | |
| 2014/0336361 A1* | 11/2014 | Giese ................... | C07K 16/468 530/387.3 |
| 2016/0229915 A1 | 8/2016 | Igawa et al. | |
| 2016/0355588 A1* | 12/2016 | Ng .......................... | A61P 35/00 |
| 2019/0248899 A1* | 8/2019 | Yan ..................... | C07K 16/2818 |
| 2020/0399373 A1 | 12/2020 | Igawa et al. | |
| 2021/0188957 A1 | 6/2021 | Kawa | |

FOREIGN PATENT DOCUMENTS

| | | |
|---|---|---|
| EP | 2289943 A1 | 3/2011 |
| EP | 2728002 A1 | 5/2014 |
| EP | 2857420 A1 | 4/2015 |
| EP | 2927321 A1 | 10/2015 |
| EP | 3050896 A1 | 8/2016 |
| EP | 3070168 A1 | 9/2016 |
| EP | 3078744 A1 | 10/2016 |
| EP | 3279216 A1 | 2/2018 |
| JP | 2009531040 A | 9/2009 |
| JP | 2013529084 A | 7/2013 |
| JP | 2013537416 A | 10/2013 |
| JP | 2015044817 A | 3/2015 |
| JP | 2016172729 A | 9/2016 |
| JP | 2018501211 A | 1/2018 |
| JP | 2018505893 A | 3/2018 |
| JP | 2018088938 A | 6/2018 |

(Continued)

OTHER PUBLICATIONS

Lloyd et al. Protein Engineering, Design & Selection 22:159-168 (Year: 2009).*
Edwards et al., J Mol Biol. 334(1): 103-118 (Year: 2003).*
Piche-Nicholas et al MABS 10(1): 81-94 (Year: 2018).*
Cochran et al., J. Immunol. Meth. 287: 147-158 (Year: 2004).*
Brinkmann et al., MAbs 9(2): 182-212 (Year: 2017).*
Maeda 2015.
Alley, S. C., et al., "Antibody-drug conjugates: targeted drug delivery for cancer," Curr Opin Chem Biol., 14:529-537 (2010).
Baeuerle, P. A., et al., "BiTE: Teaching antibodies to engage T-cells for cancer therapy," Curr Opin Mol Ther., 11(1):22-30 (2009).
Davis, J. H., et al., "SEEDbodies: fusion proteins based on strand-exchange engineered domain (SEED) $C_H3$ heterodimers in an Fc analogue platform for asymmetric binders or immunofusions and bispecific antibodies," Prot Eng Des Sel., 23(4):195-202 (2010).
De Bono, J. S., et al., "ING-1, a Monoclonal Antibody Targeting Ep-CAM in Patients with Advanced Adenocarcinomas," Clin Cancer Res., 10:7555-7565 (2004).

(Continued)

*Primary Examiner* — Phuong Huynh
(74) *Attorney, Agent, or Firm* — Nixon & Vanderhye P.C.

(57) ABSTRACT

The present invention relates to pharmaceutical compositions containing a combination of a first antigen-binding molecule and a second antigen-binding molecule, wherein the first antigen-binding molecule and the second antigen-binding molecule are not linked by a covalent bond, and they are more likely to form a heterodimer than homodimers when mixed in solution. Furthermore, the present invention relates to antigen-binding molecules, therapeutic methods, and screening methods that are associated with the combination.

21 Claims, 9 Drawing Sheets

Specification includes a Sequence Listing.

(56) References Cited

FOREIGN PATENT DOCUMENTS

| | | |
|---|---|---|
| JP | 6389093 B2 | 9/2018 |
| JP | 6667562 B2 | 3/2020 |
| JP | 6724023 B2 | 6/2020 |
| WO | WO-9627011 A1 | 9/1996 |
| WO | WO2004063351 A2 | 7/2004 |
| WO | WO-2006106905 A1 | 10/2006 |
| WO | WO2007042261 A2 | 4/2007 |
| WO | WO-2007059782 A1 | 5/2007 |
| WO | WO2007110205 A2 | 10/2007 |
| WO | WO2008119565 A2 | 10/2008 |
| WO | WO2009025846 A2 | 2/2009 |
| WO | WO-2009089004 A1 | 7/2009 |
| WO | WO2009142221 A1 | 11/2009 |
| WO | WO-2010129304 A2 | 11/2010 |
| WO | WO-2011063348 A1 | 5/2011 |
| WO | WO-2011143545 A1 | 11/2011 |
| WO | WO2012020096 A1 | 2/2012 |
| WO | WO-2012020096 A1 | 2/2012 |
| WO | WO2012088302 A2 | 6/2012 |
| WO | WO2012125850 A1 | 9/2012 |
| WO | WO2013002362 A1 | 1/2013 |
| WO | WO2013055809 A1 | 4/2013 |
| WO | WO-2013104804 A2 | 7/2013 |
| WO | WO2013180200 A1 | 12/2013 |
| WO | WO-2014084607 A1 | 6/2014 |
| WO | WO-2014087299 A1 | 6/2014 |
| WO | WO-2015046467 A1 | 4/2015 |
| WO | WO2015083764 A1 | 6/2015 |
| WO | WO2016020444 A1 | 2/2016 |
| WO | WO2016082044 A1 | 6/2016 |
| WO | WO2016130516 A1 | 8/2016 |
| WO | WO2016159213 A1 | 10/2016 |
| WO | WO2017006052 A2 | 1/2017 |
| WO | WO2017093845 A1 | 6/2017 |
| WO | WO2017159287 A1 | 9/2017 |
| WO | WO2018155611 A1 | 8/2018 |
| WO | WO2019160007 A1 | 8/2019 |
| WO | WO2020027330 A1 | 2/2020 |
| WO | WO2020045545 A1 | 3/2020 |

OTHER PUBLICATIONS

Desjarlais, J. R., et al., "Optimizing engagement of the immune system by anti-tumor antibodies: an engineer's perspective," Drug Discovery Today, 12(21/22):898-910 (2007).
Fagète, S. and Fischer, N., "Smarter Drugs—A Focus on Pan-Specific Monoclonal Antibodies," Biodrugs, 25(6):357-364 (2011).
Fan, G., et al., "Bispecific antibodies and their applications," J Hematol Oncol., 8(130), 14 pages (2015).
Ghetie, V. and Ward, E. S., "Multiple Roles for the Major Histocompatibility Complex Class I-Related Receptor FcRn," Annu Rev Immunol., 18:739-766 (2000).
Juszczak, A., et al., "Ipilimumab: a novel immunomodulating therapy causing autoimmune hypophysitis: a case report and review," Eur J Endocrinol., 167:1-5 (2012).
Kim, S. J., et al., "Antibody Engineering for the Development of Therapeutic Antibodies," Mol Cells, 20(1):17-29 (2005).
Kitazawa, T., et al., "A bispecific antibody to factors IXa and X restores factor VIII hemostatic activity in a hemophilia A model," Nat Med., 18(10):1570-1574 (2012).
Kontermann, R. E., "Dual targeting strategies with bispecific antibodies," mAbs, 4(2):182-197 (2012).
Lewis, G. D., et al., "Differential responses of human tumor cell lines to anti-p185$^{HER2}$ monoclonal antibodies," Cancer Immunol Immunother., 37:255-263 (1993).
Lutterbuese, R., et al., "T cell-engaging BiTE antibodies specific for EGFR potently eliminate KRAS- and BRAF-mutated colorectal cancer cells," PNAS, 107(28):12605-12610 (2010).
Maeda, A., et al., "Novel Antibody Modification Techniques and their Application to Antibody Therapeutics," Farumashia, 51(5):424-428 (2015).
Mazor, Y., et al., "Improving target cell specificity using a novel monovalent bispecific IgG design," mAbs, 7(2):377-389 (2015).
Mimoto, F., et al., "Fc Engineering to Improve the Function of Therapeutic Antibodies," Curr Pharmaceut Biotechnol., 17(15):1298-1314 (2016).
Pavlou, A. K. and Belsey, M. J., "The therapeutic antibodies market to 2008," Eur J Pharm Biopharmaceut., 59:389-396 (2005).
Reichert, J. M., et al., "Monoclonal antibody successes in the clinic," Nat Biotechnol., 23(9):1073-1078 (2005).
Ridgway, J. B. B., et al., "'Knobs-into-holes' engineering of antibody $C_H3$ domains for heavy chain heterodimerization," Protein Eng., 9(7):617-621 (1996).
Riechelmann, H., et al., "Phase I trial with the CD44v6-targeting immunoconjugate bivatuzumab mertansine in head and neck squamous cell carcinoma," Oral Oncol., 44:823-829 (2008).
Satoh, M., et al., "Non-fucosylated therapeutic antibodies as next-generation therapeutic antibodies," Expert Opin Biol Ther., 6(11):1161-1173 (2006).
Schaefer, G., et al., "A Two-in-One Antibody against HER3 and EGFR Has Superior Inhibitory Activity Compared with Monospecific Antibodies," Cancer Cell, 20:472-486 (2011).
Thakur, A. and Lum, L. G., "'NextGen' Biologics: Bispecific Antibodies and Emerging Clinical Results," Expert Opin Biol Ther., 16(5):675-688 (2016).
Trinh, V. A. and Hwu, W.-J., "Ipilimumab in the treatment of melanoma," Expert Opin Biol Ther., 12(6):773-782 (2012).
Wilkinson, I. C., et al., "Monovalent IgG4 molecules," mAbs, 5(3):406-417 (2013).
Adams, R., et al., "Discovery of a junctional epitope antibody that stabilizes IL-6 and gp80 protein: protein interaction and modulates its downstream signaling," Sci Rep., 7:37716 (2017).
Akter, T., et al., "Establishment of an indirect ELISA for detection of the novel antifibrotic peptide M10," PLoS One, 12(11):e0188588 (2017).
Carter, P. J. and Lazar, G. A., "Next generation antibody drugs: pursuit of the 'high-hanging fruit,'" Nat Rev Drug Discov., 17:197-223 (2018).
Chan, A. C. and Carter, P. J., "Therapeutic antibodies for autoimmunity and inflammation," Nat Rev Immunol., 10:301-316 (2010).
Elliott, J. M., et al., "Antiparallel Conformation of Knob and Hole Aglycosylated Half-Antibody Homodimers Is Mediated by a CH2—CH3 Hydrophobic Interaction," J Mol Biol., 426:1947-1957 (2014).
Hill, Z. B., et al., "Human antibody-based chemically induced dimerizers for cell therapeutic applications," Nat Chem Biol., 14:112-117 (2018).
Igawa, T., et al., "Antibody recycling by engineered pH-dependent antigen binding improves the duration of antigen neutralization," Nat Biotechnol., 28(11):1203-1207 (2010).
Ishiguro, T., et al., "An anti-glypican 3/CD3 bispecific T cell-redirecting antibody for treatment of solid tumors," Sci Transl Med., 9:eaal4291 (2017).
Liu, H., et al., "Fc Engineering for Developing Therapeutic Bispecific Antibodies and Novel Scaffolds," Front Immunol., 8:38 (2017), 15 pages.
Nazarian, A. A., et al., "Characterization of Bispecific T-cell Engager (BiTE®) Antibodies with a High-Capacity T-cell Dependent Cellular Cytotoxicity (TDCC) Assay," J Biomol Screen., 20(4):519-527 (2015).
Peggs, K. S., et al., "Cancer immunotherapy: co-stimulatory agonists and co-inhibitory antagonists," Clin Exp Immunol., 157:9-19 (2009).
Towbin, H., et al., "Sandwich immunoassay for the hapten angiotensin II," J Immunol Methods, 181:167-176 (1995).
Wozniak-Knopp, G., et al., "Introducing antigen-binding sites in structural loops of immunoglobulin constant domains: Fc fragments with engineered HER2/neu-binding sites and antibody properties," Protein Eng Des Sel., 23(4):289-297 (2010).
U.S. Appl. No. 16/968,633,371 (c) date Aug. 10, 2020, related application.
U.S. Appl. No. 17/271,239,371(c) date Feb. 25, 2021, related application.
U.S. Appl. No. 18/394,091, filed Dec. 22, 2023, Igawa et al., related application.

(56) References Cited

OTHER PUBLICATIONS

Spiess, C., et al., "Bispecific antibodies with natural architecture produced by co-culture of bacteria expressing two distinct half-antibodies," Nat Biotechnol., 31(8):753-758 (2013).

* cited by examiner

COMPOSITIONS COMPRISING ANTIGEN-BINDING MOLECULES

CROSS-REFERENCE TO RELATED APPLICATIONS

This application is a U.S. National Phase of PCT Application No. PCT/JP2018/006626, filed Feb. 23, 2018, which claims the benefit of Japanese Patent Application No. 2017-033564, filed Feb. 24, 2017, each of which is incorporated herein by reference in its entirety.

REFERENCE TO SEQUENCE LISTING SUBMITTED ELECTRONICALLY

The content of the electronically submitted listing (Name: 6663_0121_Sequence_Listing.txt, Size: 99.9 kilobytes: and Date of Creation: Aug. 21, 2019) filed with the application is incorporated herein by reference in its entirety.

TECHNICAL FIELD

The present invention relates to pharmaceutical compositions, antigen-binding molecules, therapeutic methods, and screening methods.

BACKGROUND ART

Antibodies are attracting attention as pharmaceuticals because of their high stability in plasma and few side effects. Of these, many IgG-type antibody drugs are on the market, and many antibody drugs are currently being developed (Non-patent Document 1 and Non-patent Document 2). Therapeutic antibodies are required to have functions such as blocking of interactions between specific molecules by binding to targets, and removal of target cells by antibody-dependent cellular cytotoxicity (hereinafter also referred to as ADCC) activity and complement-dependent cytotoxicity (hereinafter also referred to as CDC) activity, which are effector functions of antibody.

Native antibodies and immunoglobulins (hereinafter also referred to as IgGs) usually consist of two identical light (L) chains and two identical heavy (H) chains. The L chains and the H chains are linked by disulfide bonds, and these L chain-H chain complexes also mutually form disulfide bonds between the H chains to form a homodimer of the complexes with a molecular weight of about 150,000 Daltons. The L chains consist of an L chain variable region and an L chain constant region (hereinafter also referred to as CL), and the H chains are composed of an H chain variable region and an H chain constant region consisting of CH1, CH2, CH3, and a hinge region. The CH1 and CH2 of the H chain are separated by the hinge region, which is involved in the disulfide bonds between the H chains. IgGs having such a structure have two antigen-binding sites (bivalent antibodies).

The Fc region structurally contributes to dimer formation via the hinge region and the CH3 interface. For this reason, examples have been reported where heterodimer formation was promoted by introducing a mutation at the CH3 interface (Non-patent Documents 3, 4, and 5), and where a monovalent antibody was produced by substituting a cysteine residue in the hinge region with another amino acid and introducing a modification that inhibits CH3 dimer formation (Non-patent Document 6).

In terms of function, the Fc region also contributes to prolongation of retention in blood by interaction with neonatal Fc receptor (hereinafter also referred to as FcRn) (Non-patent Document 7), and is involved in expression of effector functions such as Fc receptor-mediated ADCC, CDC, and antibody-dependent cell-mediated phagocytosis (ADCP). In recent years, modification techniques for improving effector functions have also been reported (Non-patent Document 8) and utilized for enhancing the drug efficacy of antibody drugs.

Antibody molecules bind to antigens expressed on cancer cells, and exert cytotoxic activity against cancer cells by ADCC or such. It is known that such cytotoxic activity by ADCC or such depends on the number of antigens expressed on cells targeted by the therapeutic antibody (Non-patent Document 9), and therefore, from the viewpoint of the effect of a therapeutic antibody, it is preferable that the target antigen is expressed in high amounts. However, even if the expression level of the antigen is high, if the antigen is expressed in normal tissues, side effects are a serious problem since cytotoxic activities such as ADCC will be exerted on normal cells. Therefore, it is preferable that the antigen targeted by a therapeutic antibody as a cancer therapeutic agent is specifically expressed in cancer cells. For example, although an antibody molecule against the EpCAM antigen, known as a cancer antigen, was considered to be a promising cancer therapeutic agent, it is known that the EpCAM antigen is also expressed in the pancreas, and in fact, administration of an anti-EpCAM antibody has been reported to cause pancreatitis as a side effect in clinical trials due to cytotoxic activity against the pancreas (Non-patent Document 10).

Encouraged by the success of antibody drugs that exert cytotoxic activity by ADCC activity, second-generation improved antibody molecules have been reported which exhibit potent cytotoxic activity by enhancement of ADCC activity by removing fucose of N-type sugar chains in the Fc region of native human IgG1 (Non-patent Document 11), or by enhancement of ADCC activity by enhancing the binding to FcγRIIIa through amino acid substitution of the Fc region of wild-type human IgG1 (Non-patent Document 12) and the like. As antibody drugs that exert cytotoxic activity on cancer cells by mechanisms other than the above-mentioned NK cell-mediated ADCC activity, antibody drug conjugates (ADCs) which are conjugates of antibodies with drugs having potent cytotoxic activity (Non-patent Document 13), and modified antibody molecules that exhibit more potent cytotoxic activity such as low molecular weight antibodies that exert cytotoxic activity on cancer cells by recruiting T cells to cancer cells (Non-patent Document 14) have been reported.

Such antibody molecules that exert more potent cytotoxic activity are able to exert cytotoxic activity against cancer cells having not much expression of antigens, but on the other hand, they also exert cytotoxic activity against normal tissues with less antigen expression. Actually, as compared to Cetuximab, which is native human IgG1 against the EGFR antigen, an anti-CD3 and anti-EGFR bispecific antibody EGFR-BiTE can exhibit potent cytotoxic activity and anti-tumor effect against cancer cells by recruiting T cells to cancer cells. On the other hand, administration of EGFR-BiTE to cynomolgus monkeys has also been found to cause serious side effects since EGFR is also expressed in normal tissues (Non-patent Document 15). Furthermore, bivatuzumab mertansine, which is an ADC in which mertansine is conjugated to an antibody against CD44v6, which is highly expressed in cancer cells, has been found to have serious skin toxicity and hepatotoxicity in clinical practice as CD44v6 is also expressed in normal tissues (Non-patent Document 16).

Therefore, when using an antibody capable of exerting potent cytotoxic activity even against cancer cells with low antigen expression, it is necessary for the target antigen to be expressed in a highly cancer-specific manner. However, the number of cancer antigens expressed extremely specifically in cancer is thought to be limited, as is seen by the fact that HER2, which is the target antigen of Herceptin, and EGFR, which is the target antigen of Cetuximab, are also expressed in normal tissues. Therefore, while it is possible to enhance cytotoxic activity against cancer, side effects due to cytotoxic effects on normal tissues can be problematic.

Recently, it has been shown that Ipilimumab, which enhances tumor immunity by inhibiting CTLA4, which contributes to immunosuppression in cancer, prolongs overall survival against metastatic melanoma (Non-patent Document 17). However, since Ipilimumab systemically inhibits CTLA4, while tumor immunity is enhanced, the issue is that it shows severe side-effects like autoimmune disease due to systemic activation of immunity (Non-patent Document 18).

Various technologies have been developed as technologies applicable to second-generation antibody drugs, and techniques and such have been reported for improving effector functions, antigen-binding ability, pharmacokinetics, or stability or reducing immunogenicity risk. (Non-patent Document 19). However, there have been not many reports of a technology for resolving the side effects described above, that would enable antibody drugs to act on target tissue with high specificity.

As a technique for imparting high selectivity, a strategy to aim at two different targets at the same time has been reported (Non-patent Documents 20, 21, 22, and 23).

Studies of bispecific antibodies using CD4 and CD70 double-positive cells and HER2 and EGFR double-positive cells have shown improved cytotoxic activity by about ten times as compared to when using single positive cells (Non-patent Documents 24 and 25).

Amid such circumstances, various techniques relating to methods for producing bispecific antibodies have been developed in recent years (Patent Documents 1 to 6).

CITATION LIST

Patent Documents

[Patent Document 1] WO96/027011
[Patent Document 2] WO2006/106905
[Patent Document 3] WO2009/089004
[Patent Document 4] WO2010/129304
[Patent Document 5] WO2011/143545]
[Patent Document 6] WO2014/084607

Non-Patent Documents

[Non-patent Document 1] Monoclonal antibody successes in the clinic. Janice M Reichert, Clark J Rosensweig, Laura B Faden & Matthew C Dewitz, Nat. Biotechnol. (2005) 23, 1073-1078
[Non-patent Document 2] The therapeutic antibodies market to 2008. Pavlou A K, Belsey M J., Eur. J. Pharm. Biopharm. (2005) 59 (3), 389-396
[Non-patent Document 3] 'Knobs-into-hole' engineering of antibody CH3 domains for heavy chain heterodimerization. Ridgway J B, Presta L G, Carter P, Protein Eng. (1996) 9 (7), 617-621
[Non-patent Document 4] SEEDbodies: fusion based on strand-exchange engineered domain (SEED) CH3 heterodimers in an Fc analogue platform for asymmetric binders or immunofusions and bispecific antibodies. Davis J H, Aperlo C, Li Y, Kurosawa E, Lan Y, Lo K M, Huston J S, Protein Eng. Des. Sel. (2010) 23 (4) 195-202
[Non-patent Document 5] A bispecific antibody to factor IXa and X restores factor VIII hemostatic activity in an hemophilia A model. Kitazawa T, Igawa T, Sampei Z, Muto A, Kojima T, Soeda T, Yoshihashi K, Okuyama-Nishida Y, Saito H, Tshunoda H, Suzuki T, Adachi H, Miyazaki T, Ishii S, Kamata-Sakurai M, Iida T, Harada A, Esaki K, Funaki M, Moriyama C, Tanaka E, Kikuchi Y, Wakabayashi T, Wada M, Goto M, Toyoda T, Ueyama A, Suzuki S, Haraya K, Tachibana T, Kawabe Y, Shima M, Yoshioka A, Hattori K, Nat. Med. (2012) 18 (10) 1570-1574
[Non-patent Document 6] Monovalent IgG4 molecules Immunoglobulin Fc mutations that result in a monomeric structure. Wilkinson I C, Fowler S B, Machiesky L, Miller K, Adib M, Her C, Borrok M J, Tsui P, Burrell M, Corkill D J, Witt S, Lowe D C, Webster C I, mAbs (2013) 5 (3) 406-417
[Non-patent Document 7] Multiple roles for the major histocompatibility complex class I-related receptor FcRn. Ghetie V, Ward S, Annu. Rev. Immunol. (2000) 18, 739-766
[Non-patent Document 8] Fc engineering to improve the function of therapeutic antibodies. Mimoto F, Kuramochi T, Katada H, Igawa T, Hattori K, Curr. Pharm. Biotech. (2012) 7 1444-1450
[Non-patent Document 9] Differential responses of human tumor cell lines to anti-p185HER2 monoclonal antibodies. Lewis G D, Figari I, Fendly B, Wong W L, Carter P, Gorman C, Shepard H M, Cancer Immunol. Immunother. (1993) 37, 255-263
[Non-patent Document 10] ING-1, a monoclonal antibody targeting Ep-CAM in patients with advanced adenocarcinomas. de Bono J S, Tolcher A W, Forero A, Vanhove G F, Takimoto C, Bauer R J, Hammond L A, Patnaik A, White M L, Shen S, Khazaeli M B, Rowinsky E K, LoBuglio A F, Clin. Cancer Res. (2004) 10 (22), 7555-7565
[Non-patent Document 11] Non-fucosylated therapeutic antibodies as next-generation therapeutic antibodies. Satoh M, Iida S, Shitara K., Expert Opin. Biol. Ther. (2006) 6 (11), 1161-1173
[Non-patent Document 12] Optimizing engagement of the immune system by anti-tumor antibodies: an engineer's perspective. Desjarlais J R, Lazar G A, Zhukovsky E A, Chu S Y., Drug Discov. Today (2007) 12 (21-22), 898-910
[Non-patent Document 13] Antibody-drug conjugates: targeted drug delivery for cancer. Alley S C, Okeley N M, Senter P D., Curr. Opin. Chem. Biol. (2010) 14 (4), 529-537
[Non-patent Document 14] BITE: Teaching antibodies to engage T-cells for cancer therapy. Baeuerle P A, Kufer P, Bargou R., Curr. Opin. Mol. Ther. (2009) 11 (1), 22-30
[Non-patent Document 15] T cell-engaging BiTE antibodies specific for EGFR potently eliminate KRAS- and BRAF-mutated colorectal cancer cells. Lutterbuese R, Raum T. Kischel R, Hoffmann P, Mangold S, Rattel B, Friedrich M, Thomas O, Lorenczewski G, Rau D, Schaller E, Herrmann I, Wolf A, Urbig T, Baeuerle P A, Kufer P., Proc. Natl. Acad. Sci. U.S.A. (2010) 107 (28), 12605-12610

[Non-patent Document 16] Phase I trial with the CD44v6-targeting immunoconjugate bivatuzumab mertansine in head and neck squamous cell carcinoma. Riechelmann H, Sauter A, Golze W, Hanft G, Schroen C, Hoermann K, Erhardt T, Gronau S., Oral Oncol. (2008) 44 (9), 823-829

[Non-patent Document 17] Ipilimumab in the treatment of melanoma. Trinh V A, Hwu W J. Expert Opin. Biol. Ther., (2012) 12 (6), 773-782

[Non-patent Document 18] IPILIMUMAB—A NOVEL IMMUNOMODULATING THERAPY CAUSING AUTOIMMUNE HYPOPHYSITIS: A CASE REPORT AND REVIEW. Juszczak A, Gupta A, Karavitaki N, Middleton M R, Grossman A., Eur. J. Endocrinol. (2012) 167 (1), 1-5

[Non-patent Document 19] Antibody engineering for the development of therapeutic antibodies. Kim S J, Park Y, Hong H J, Mol. Cells. (2005) 20 (1), 17-29

[Non-patent Document 20] Dual targeting strategies with bispecific antibodies. Kontermann R E. MAbs (2012) 4 (2), 182-97

[Non-patent Document 21] Smarter drugs: a focus on pan-specific monoclonal antibodies. Fagete S, Fischer N, BioDrugs (2011) 25 (6), 357-364

[Non-patent Document 22] "NextGen" Biologics: Bispecific Antibodies and Emerging Clinical Results. Thakur A, Lum L G, Expert Opin. Biol. Ther. 2016 16 (5), 675-688.

[Non-patent Document 23] Bispecific antibodies and their applications. Fan G, Wang Z, Hao M, Li J. J Hematol Oncol. (2015) 8:130.

[Non-patent Document 24] A two-in-one antibody against HER3 and EGFR has superior inhibitory activity compared with monospecific antibodies. Schaefer G, Haber L, Crocker L M, Shia S, Shao L, Dowbenko D, Totpal K, Wong A, Lee C V, Stawicki S, Clark R, Fields C, Lewis Phillips G D, Prell R A, Danilenko D M, Franke Y, Stephan J P, Hwang J, Wu Y, Bostrom J, Sliwkowski M X, Fuh G, Eigenbrot C. Cancer Cell. (2011) 20 (4), 472-486.

[Non-patent Document 25] Improving target cell specificity using a novel monovalent bispecific IgG design. Mazor Y, Oganesyan V, Yang C, Hansen A, Wang J, Liu H, Sachsenmeier K, Carlson M, Gadre D V, Borrok M J, Yu X Q, Dall'Acqua W, Wu H, Chowdhury P S. MAbs. (2015) 7 (2), 377-389.

SUMMARY OF THE INVENTION

Problems to be Solved by the Invention

Under the circumstances where the utility of bispecific antibodies is increasingly anticipated as described above, antibodies whose effector function is more highly specific for cells involved in disease than normal cells, and as a result, have highly reduced side effects are desired.

Means for Solving the Problems

The present inventors created a combination of antigen-binding molecules that exist separately as antibody-half molecules without interaction when present in plasma in a non-antigen-bound state, but form a bispecific antibody on target cell surface, which led to the completion of the present invention. Examples of embodiments of the present invention are the following [1] to [15].

[1] a pharmaceutical composition, comprising
a first antigen-binding molecule having a first antigen-binding region that binds to a first antigen and a first polypeptide comprising either or both of a first CH2 and a first CH3, and
a second antigen-binding molecule having a second antigen-binding region that binds to a second antigen and a second polypeptide comprising either or both of a second CH2 and a second CH3,
wherein said first antigen-binding molecule and said second antigen-binding molecule are not linked by a covalent bond and are more likely to form a heterodimer than a homodimer when mixed in solution;

[2] the composition according to [1], wherein, when a sensor chip on which 50 pg per $mm^2$ of the first antigen-binding molecule is immobilized and a measurement solution containing 2.5 mg/mL of the second antigen-binding molecule are used in surface plasmon resonance to measure affinity between the two antigen-binding molecules, the binding amount of the second antigen-binding molecule to the first antigen-binding molecule is within the range of 1:0.1 to 1:0.9 in terms of molar ratio;

[3] the composition according to [1] or [2], wherein the amount of the heterodimer formed under conditions in which cells expressing the first antigen and the second antigen are present is higher than that under conditions in which the cells are not present;

[4] the composition according to any one of [1] to [3], wherein the binding activity of the heterodimer to FcγR when said heterodimer is formed is higher than the binding activity of a monomer of the first antigen-binding molecule or a monomer of the second antigen-binding molecule to FcγR, or the binding activity of the homodimer to FcγR when said homodimer is formed;

[5] the composition according to any one of [1] to [4], wherein the first polypeptide comprises the first CH3 and the second polypeptide comprises the second CH3, and wherein the first CH3 and the second CH3 have at least one modification of (i) to (iii) below to make the first antigen-binding molecule and the second binding-molecule more likely to form the heterodimer than the homodimer when mixed in solution:
(i) a modification where either of the first CH3 and the second CH3 has a positively-charged region and the other has a negatively-charged region, and when the heterodimer is formed, the positively-charged region interacts with the negatively-charged region,
(ii) a modification where either of the first CH3 and the second CH3 has a convex portion and the other has a concave portion, and when the heterodimer is formed, the convex portion fits into and interacts with the concave portion, and
(iii) a modification where the first CH3 and the second CH3 are modified IgG CH3, a part of which is replaced with a part of IgA CH3, and when said heterodimer is formed, the replaced part of IgA CH3 in said first CH3 interacts with the replaced part of IgA CH3 in said second CH3;

[6] the composition according to any one of [1] to [5], wherein either or both of said first CH3 and said second CH3 further have a substitution of at least one of the amino acid residues at positions 357, 397, and 409 in the EU numbering system with another amino acid residue;

[7] the composition according to any one of [1] to [6], wherein either or both of said first polypeptide and said second polypeptide further comprise a hinge region portion in an antibody-half molecule;

[8] the composition of [7], wherein said hinge region portion in either or both of said first polypeptide and said second polypeptide has a modification of the cysteine residues at either or both of positions 226 and 229 in the EU numbering system to another amino acid residue;

[9] the composition according to any one of [1] to [8], wherein said first polypeptide and said second polypeptide each comprises a constant region portion in an antibody-half molecule;

[10] the composition according to any one of [1] to [9], wherein the effector function under conditions in which cells expressing said first antigen and said second antigen are present is higher than that under conditions in which cells expressing said first antigen but not the second antigen or cells expressing said second antigen but not the first antigen are present;

[11] a pharmaceutical composition, comprising
a first antigen-binding molecule having a first antigen-binding region that binds to a first antigen and a first polypeptide comprising a first CH3, and
a second antigen-binding molecule having a second antigen-binding region that binds to a second antigen and a second polypeptide comprising a second CH3,
wherein said first antigen-binding molecule and said second antigen-binding molecule are not linked by a covalent bond, and
wherein said first CH3 and said second CH3 have at least one modification of (iv) to (vi) below:
(iv) a modification where either of said first CH3 and said second CH3 has a positively-charged region and the other has a negatively-charged region, and when the heterodimer is formed, the positively-charged region interacts with the negatively-charged region,
(v) a modification where either of said first CH3 and said second CH3 has a convex portion and the other has a concave portion, and when the heterodimer is formed, the convex portion fits into and interacts with the concave portion, and
(vi) a modification where said first CH3 and said second CH3 are modified IgG CH3 a part of which is replaced with a part of IgA CH3, and when said heterodimer is formed, the replaced part of IgA CH3 in said first CH3 interacts with the replaced part of IgA CH3 in said second CH3;

[12] a first antigen-binding molecule comprising a first antigen-binding region that binds to a first antigen and a first polypeptide comprising either or both of a first CH2 and a first CH3, wherein, when mixed in solution with a second antigen-binding molecule having a second antigen-binding region that binds to a second antigen and a second polypeptide comprising either or both of a second CH2 and a second CH3, the first antigen-binding molecule is more likely to form a heterodimer with the second antigen-binding molecule than a homodimer of the first antigen-binding molecule, and wherein in said heterodimer, said first antigen-binding molecule and said second antigen-binding molecule are not linked by a covalent bond;

[13] a second antigen-binding molecule comprising a second antigen-binding region that binds to a second antigen and a second polypeptide comprising either or both of a second CH2 and a second CH3, wherein, when mixed in solution with a first antigen-binding molecule having a first antigen-binding region that binds to a first antigen and a first polypeptide comprising either or both of a first CH2 and a first CH3, the second antigen-binding molecule is more likely to form a heterodimer with the first antigen-binding molecule than a homodimer of the second antigen-binding molecule, and wherein in said heterodimer, said first antigen-binding molecule and said second antigen-binding molecule are not linked by a covalent bond;

[14] a method for treating a disease caused by a pathogenic cell in a subject, wherein
a first antigen-binding molecule having a first antigen-binding region that binds to a first antigen and a first polypeptide comprising either or both of a first CH2 and a first CH3, and
a second antigen-binding molecule having a second antigen-binding region that binds to a second antigen and a second polypeptide comprising either or both of a second CH2 and a second CH3
are administered simultaneously or sequentially to a subject having a pathogenic cell that expresses the first antigen and the second antigen, and wherein said first antigen-binding molecule and said second antigen-binding molecule are not linked by a covalent bond before and after administration and form a heterodimer on the surface of said pathogenic cell to exert an effector function; and

[15] a method of selecting a combination of a first antigen-binding molecule and a second antigen-binding molecule from a group of variants of a first antigen-binding molecule having a first antigen-binding region that binds to a first antigen and a first polypeptide comprising either or both of a first CH2 and a first CH3, and a group of variants of a second antigen-binding molecule having a second antigen-binding region that binds to a second antigen and a second polypeptide comprising either or both of a second CH2 and a second CH3,
wherein the combination is one where,
(a) the first antigen-binding molecule and the second antigen-binding molecule are not linked by a covalent bond,
(b) the first antigen-binding molecule and the second antigen-binding molecule are more likely to form a heterodimer between the first antigen-binding molecule and the second antigen-binding molecule than a homodimer of the first antigen-binding molecule or a homodimer of the second antigen-binding molecule, and
(c) when a sensor chip on which 50 pg per $mm^2$ of the first antigen-binding molecule is immobilized and a measurement solution containing 2.5 mg/mL of the second antigen-binding molecule are used in surface plasmon resonance to measure affinity between the two antigen-binding molecules, the binding amount of the second antigen-binding molecule to the first antigen-binding molecule is within the range of 1:0.1 to 1:0.9 in terms of molar ratio.

Effects of the Invention

The present invention provides combinations of antigen-binding molecules with reduced side effects.

BRIEF DESCRIPTION OF THE DRAWINGS

FIG. 1-2 is a continuation of FIG. 1-1.

FIG. 1-3 is a continuation of FIG. 1-2.

FIG. 2 shows the result of ADCC reporter assay by which ADCC activity by a combination of antibody-half molecules was examined in the presence of cells expressing two different antigens (EREG_SK-pca60_#2) or in the presence of cells expressing one antigen (SK-pca60 or SKE-4B2).

FIG. 3 shows changes in blood concentration in normal mice of antibody-half molecules or a whole antibody having a variable region for mouse CD19.

FIG. 5-1 is a set of graphs showing the result of confirming whether or not antibody-half molecules form dimers (whole antibodies) by size exclusion chromatography. W and H represent the elution positions of the whole antibodies and the antibody-half molecules, respectively.

FIG. 5-2 is a continuation of FIG. 5-1.

MODES FOR CARRYING OUT THE INVENTION

A. Definitions

Figure 1:
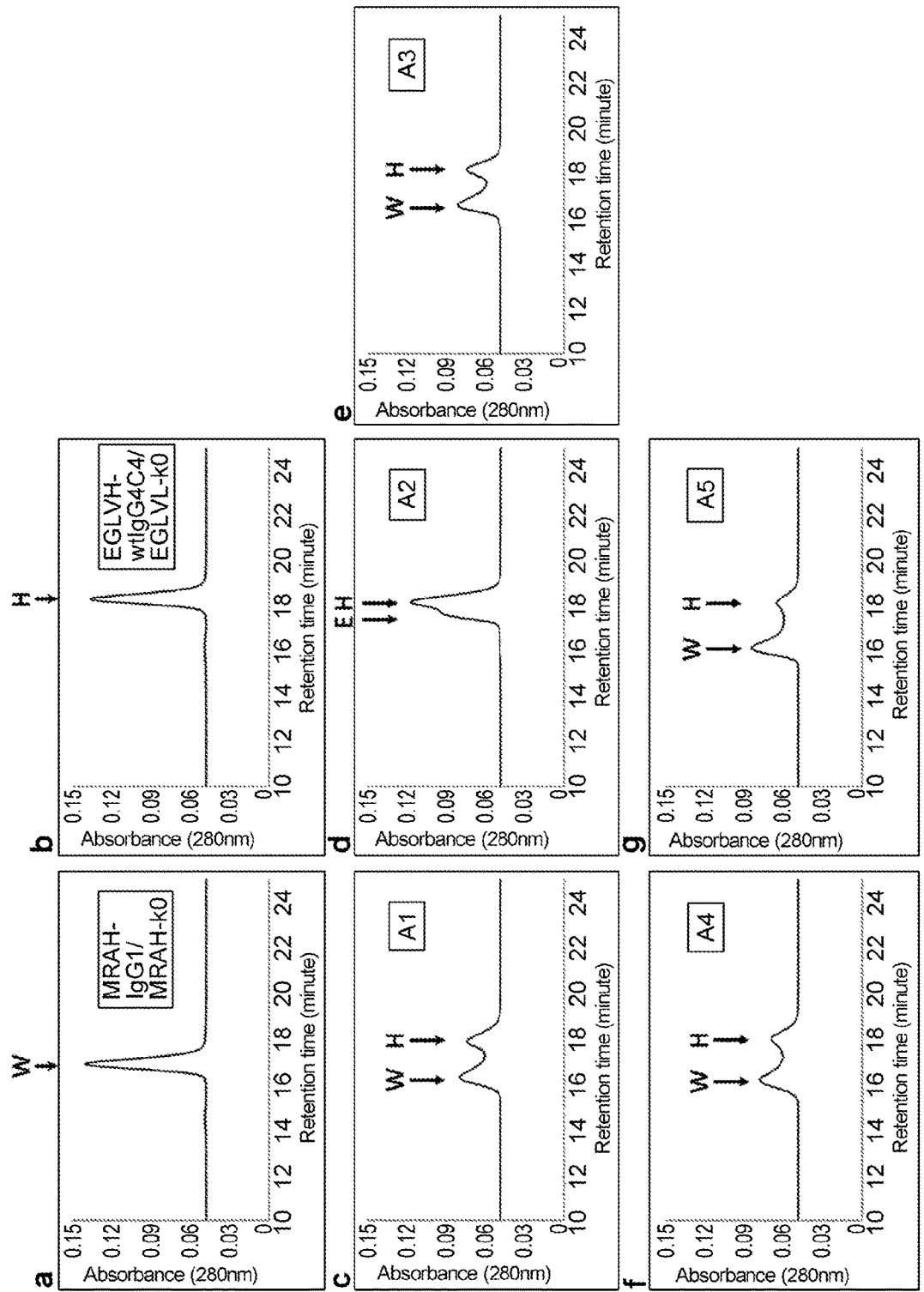
FIG. 1-1 is a set of graphs showing the result of confirming whether or not antibody-half molecules form dimers (whole antibodies) by size exclusion chromatography. W and H represent the elution positions of the whole antibodies and the antibody-half molecules, respectively, and E represents the elution position of the molecular state presumed to be in equilibrium between the whole antibodies and the antibody-half molecules.
Figures 1, 2:
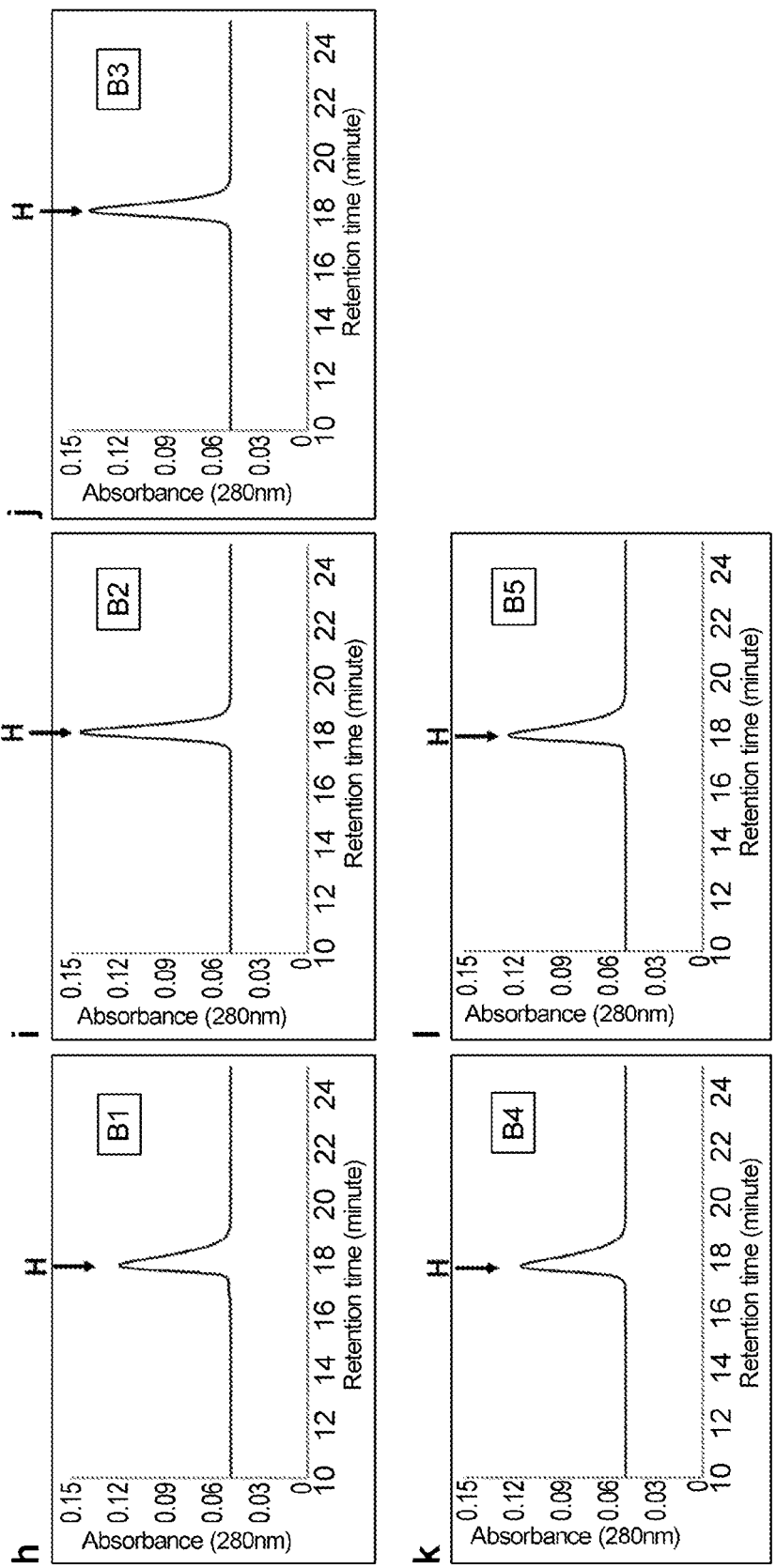

Herein, the term "polypeptide" encompasses all peptides with a plurality of amino acids linked by peptide bonds. Herein, polypeptides are sometimes referred to as "peptides" or "proteins."

Herein, the term "antigen-binding region" means a compound having an activity of binding to an antigen. The antigen-binding region may be peptidic or non-peptidic.

Herein, "CH1" means a single polypeptide chain of CH1 of an antibody. Specifically, CH1 is a region represented by amino acid residues at positions 118 to 215 of an H chain in the EU numbering system, and herein encompasses the wild-type and also variants produced by introducing amino acid residue substitutions, additions, or deletions into the wild-type.

Herein, "CH2" means a single polypeptide chain of CH2 of an antibody. Specifically, CH2 is a region represented by amino acid residues at positions 231 to 340 of an H chain in the EU numbering system, and herein encompasses the wild-type and also variants produced by introducing amino acid residue substitutions, additions, or deletions into the wild-type.

Herein, "CH3" means a single polypeptide chain of CH3 of an antibody. Specifically, CH3 is a region represented by amino acid residues from position 341 to the C-terminus of an H chain in the EU numbering system, and herein encompasses the wild-type and also variants produced by introducing amino acid residue substitutions, additions, or deletions into the wild-type.

Herein, "CL" means a single polypeptide chain of CL of an antibody. Specifically, CL is a region represented by amino acid residues from position 108 to the C-terminus of an L chain in the EU numbering system, and herein encompasses the wild-type and also variants produced by introducing amino acid residue substitutions, additions or deletions into the wild-type.

Herein, "antibody-half molecule" means a single molecule when the binding between H chains in an antibody is dissociated, and is sometimes generally called a monovalent antibody. Examples of an antibody-half molecule in the case where the antibody is IgG include a complex composed of one H chain and one L chain. Antibody-half molecules include molecules consisting of one H chain which are produced by dissociating the inter-H chain bonds of so-called heavy chain antibodies (also called VHHs (VH originating from heavy-chain antibody)), which are antibodies consisting of two H chains found in camelid antibodies and such.

In one embodiment, the antibody-half molecules include those derived from chimeric antibodies or humanized antibodies.

In one embodiment, the antibody-half molecules include those derived from various isotypes such as IgG, IgM, IgA, IgD, and IgE. The antibody-half molecules are preferably those derived from IgG. There are IgG1, IgG2, IgG3, and IgG4 in IgG. The antibody-half molecules may be derived from any of these subtypes. The antibody-half molecules are preferably derived from IgG1 or IgG2 from the viewpoint of easily exerting effector function.

A "hinge region" as used herein is a region located between CH1 and CH2 in an antibody. Specifically, the hinge region is a region represented by amino acid residues at positions 216 to 230 in the EU numbering system, and herein encompasses the wild-type and also variants produced by introducing amino acid residue substitutions, additions, or deletions into the wild-type. Herein, the "hinge region portion in an antibody-half molecule" means a hinge region portion in one H chain, and it means a portion consisting of a single chain polypeptide.

Herein, a "constant region" is a region including CH1, CH2, CH3, CL, and a hinge region in an antibody. Herein, a "constant region portion in an antibody-half molecule" means a constant region portion in an antibody-half molecule.

The term "Fc region" herein is used to define a C-terminal region of an immunoglobulin H chain that contains at least a portion of the constant region. The term includes native sequence Fc regions and variant Fc regions. In one embodiment, a human IgG H chain Fc region extends from Cys226, or from Pro230, to the carboxyl-terminus of the H chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc receptor" or "FcR" refers to a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "covalent bond" herein includes all those generally known. "Covalent bonds" includes, for example, disulfide bonds and carbon-carbon bonds.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$p, $^{212}$Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

B. Pharmaceutical Compositions

In one aspect, the present invention provides pharmaceutical compositions comprising either or both of a first antigen-binding molecule and a second antigen-binding molecule.

1. First Antigen-Binding Molecule

The first antigen-binding molecule has a first antigen-binding region and a first polypeptide.

a. First Antigen-Binding Region

The first antigen-binding region is a region that binds to a first antigen. Preferably, the first antigen-binding region comprises the variable region portion of an antibody-half molecule or a first antigen-binding fragment thereof. The first antigen-binding fragment means a fragment of the variable region portion of an antibody-half molecule that retains the ability to bind to the first antigen.

The first antigen includes, for example, a protein expressed on a target cell. The protein is preferably an antigen expressed on abnormal cells causing a target disease. The antigen expressed on abnormal cells is preferably a membrane protein. The membrane protein is preferably an extracellular region thereof.

The first antigen may be the same as or different from a second antigen described later on. Preferably, the first antigen and the second antigen are different. As a result of the difference between the first antigen and the second antigen, the target specificity of the combination of the first antigen-binding molecule and the second antigen-binding molecule to abnormal cells is improved.

Preferably, either or both of the first antigen and the second antigen are expressed on abnormal cells but not on normal cells, more preferably, both the first antigen and the second antigen are expressed on abnormal cells but not on normal cells.

The type of antigens is not particularly limited, and any type of antigen can be used. Examples of antigens include receptors or their fragments, cancer antigens, MHC antigens, and differentiation antigens and the like, but are not particularly limited thereto.

Examples of the receptors include receptors belonging to the hematopoietic factor receptor family, cytokine receptor family, tyrosine kinase-type receptor family, serine/threonine kinase-type receptor family, TNF receptor family, G protein-coupled receptor family, GPI-anchored receptor family, tyrosine phosphatase-type receptor family, adhesion factor family, hormone receptor family, and such. Reports on the receptors belonging to these receptor families and their characteristics can be found in various sources of documents, for example, in Cooke B A., King R J B., van der Molen H J. ed. New Comprehensive Biochemistry Vol. 18B "Hormones and their Actions Part II" pp. 1-46 (1988) Elsevier Science Publishers BV., New York, USA; Patthy L. (1990) Cell, 61: 13-14; Ullrich A., et al. (1990) Cell, 61: 203-212; Massagul J. (1992) Cell, 69: 1067-1070; Miyajima A., et al. (1992) Annu. Rev. Immunol., 10: 295-331; Taga T. and Kishimoto T. (1992) FASEB J., 7: 3387-3396; Fantl W I., et al. (1993) Annu. Rev. Biochem., 62: 453-481; Smith C A., et al. (1994) Cell, 76: 959-962; Flower D R. (1999) Biochim. Biophys. Acta, 1422: 207-234; Miyasaka M. ed. Cell Technology, Handbook Series "Handbook for adhesion factors" (1994) Shujunsha, Tokyo, Japan; and such. Examples of specific receptors belonging to the above-mentioned receptor families include human or mouse erythropoietin (EPO) receptor, human or mouse granulocyte-colony stimulating factor (G-CSF) receptor, human or mouse thrombopoietin (TPO) receptor, human or mouse insulin receptor, human or mouse Flt-3 ligand receptor, human or mouse platelet-derived growth factor (PDGF) receptor, human or mouse interferon (IFN)-α or -β receptor, human or mouse leptin receptor, human or mouse growth hormone (GH) receptor, human or mouse interleukin (IL)-10 receptor, human or mouse insulin-like growth factor (IGF)-I receptor, human or mouse leukemia inhibitory factor (LIF) receptor, and human or mouse ciliary neurotrophic factor (CNTF) receptor (hEPOR: Simon, S. et al. (1990) Blood 76, 31-35; mEPOR: D'Andrea, A D. et al. (1989) Cell 57, 277-285; hG-CSFR: Fukunaga, R. et al. (1990) Proc. Natl. Acad. Sci. USA. 87, 8702-8706; mG-CSFR: Fukunaga, R. et al. (1990) Cell 61, 341-350; hTPOR: Vigon, I. et al. (1992) 89, 5640-5644.; mTPOR: Skoda, R C. et al. (1993) 12, 2645-2653; hInsR: Ullrich, A. et al. (1985) Nature 313, 756-761; hFlt-3: Small, D. et al. (1994) Proc. Natl. Acad. Sci. USA. 91, 459-463; hPDGFR: Gronwald, R G K. et al. (1988) Proc. Natl. Acad. Sci. USA. 85, 3435-3439; hIFN a/B R: Uze, G. et al. (1990) Cell 60, 225-234; and Novick, D. et al. (1994) Cell 77, 391-400).

Cancer antigens are antigens that are expressed as cells become malignant, and are also called tumor-specific antigens. Furthermore, abnormal sugar chains that appear on cell surfaces and protein molecules when the cells become cancerous are also cancer antigens and are specifically called as carcinoma associated carbohydrate antigen. Examples of cancer antigens include CA19-9, CA15-3, and sialyl SSEA-1 (SLX).

MHC antigens can be classified broadly into MHC class I antigens and MHC class II antigens: MHC class I antigens include HLA-A, -B, -C, -E, -F, -G, and -H; and MHC class II antigens include HLA-DR, -DQ, and -DP.

Differentiation antigens include CD1, CD2, CD3, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

b. First Polypeptide

The first polypeptide comprises either or both of a first CH2 and a first CH3. The first polypeptide preferably comprises a first CH3.

In one embodiment, the first polypeptide may further comprise a hinge region portion in an antibody-half molecule. In this embodiment, the first polypeptide may comprise an Fc region portion in an antibody-half molecule.

In another embodiment, the first polypeptide may further comprise CH1 in an antibody-half molecule. In this embodiment, the first polypeptide may further comprise CL in an antibody-half molecule. In this embodiment, the first polypeptide may comprise a constant region portion in an antibody-half molecule. The constant region portion includes the Fc region portion.

When the first polypeptide includes an Fc region portion or a constant region portion in an antibody-half molecule, modifications that improve or decrease their inherent effector function may be further added to the Fc region portion or the constant region portion.

Specifically, such modifications include modifications that enhance or decrease binding affinity to FcγR, FcRn, or C1q, but are not limited thereto.

c. Other Parts

The first antigen-binding molecule may have a compound other than the above-mentioned first antigen-binding region and first polypeptide. "A compound other than the first antigen-binding region and the first polypeptide" includes, for example, peptidic or non-peptidic linkers, and other compounds. Examples of other compounds include peptidic or non-peptidic cytotoxic agents.

2. Second Antigen-Binding Molecule

The second antigen-binding molecule has a second antigen-binding region and a second polypeptide.

a. Second Antigen-Binding Region

The second antigen-binding region is a region that binds to a second antigen. Preferably, the second antigen-binding region comprises a variable region portion of an antibody-half molecule or a second antigen-binding fragment thereof. The second antigen-binding fragment means a fragment of the variable region portion of an antibody-half molecule that retains its ability to bind to the second antigen.

The second antigen includes, for example, a protein expressed on a target cell. The protein is preferably an antigen expressed on abnormal cells causing a target disease. The antigen expressed on abnormal cells is preferably a membrane protein. The membrane protein is preferably an extracellular region thereof.

The second antigen may be the same as or different from the above-mentioned first antigen. Preferably, the first antigen and the second antigen are different. As a result of the difference between the first antigen and the second antigen, the target specificity of the combination of the first antigen-binding molecule and the second antigen-binding molecule to abnormal cells is improved.

Preferably, either or both of the first antigen and the second antigen are expressed on abnormal cells but not on normal cells, more preferably, both the first antigen and the second antigen are expressed on abnormal cells but not on normal cells.

b. Second Polypeptide

The second polypeptide comprises either or both of a second CH2 and a second CH3. The second polypeptide preferably comprises a second CH3.

In one embodiment, the second polypeptide may further comprise a hinge region portion in an antibody-half molecule. In this embodiment, the second polypeptide may comprise an Fc region portion in an antibody-half molecule.

In another embodiment, the second polypeptide may further comprise CH1 in an antibody-half molecule. In this embodiment, the second polypeptide may further comprise CL in an antibody-half molecule. In this embodiment, the second polypeptide may comprise a constant region portion in an antibody-half molecule. The constant region portion includes the Fc region portion.

When the second polypeptide includes an Fc region portion or a constant region portion in an antibody-half molecule, modifications that improve or decrease their inherent effector function may be further added to the Fc region portion or the constant region portion. Specifically, such modifications include modifications that enhance or decrease binding affinity to FcγR, FcRn, or C1q, but are not limited thereto.

c. Other Parts

The second antigen-binding molecule may have a compound other than the above-mentioned second antigen-binding region and second polypeptide. "A compound other than the second antigen-binding region and the second polypeptide" includes, for example, peptidic or non-peptidic linkers, and other compounds. Examples of other compounds include peptidic or non-peptidic cytotoxic agents.

3. Relationship Between the First Antigen-Binding Molecule and the Second Antigen-Binding Molecule The first antigen-binding molecule and the second antigen-binding molecule are not linked by a covalent bond. In the pharmaceutical composition, the first antigen-binding molecule and the second antigen-binding molecule may interact unless linked by a covalent bond. Examples of such interactions that do not depend on covalent bonds include hydrogen bonding and intermolecular bonding. The amount of such interaction is preferably small. The smaller the amount, the more the side effects are reduced.

In one embodiment, the molar ratio of the amount of binding between the first antigen-binding molecule and the second antigen-binding molecule measured by surface plasmon resonance can be used as an indicator of the interaction. For example, when the affinity between the two antigen-binding molecules is measured in surface plasmon resonance using a sensor chip on which 50 pg of the first antigen-binding molecule is immobilized per 1 mm$^2$ and a measurement solution containing 2.5 mg/mL of the second antigen-binding molecule, the binding amount of the second antigen-binding molecule to the first antigen-binding molecule is within the range of 1:0.1 to 1:0.9 in terms of molar ratio.

As the upper limit value of the binding amount of the second antigen-binding molecule, the molar ratio may be 1:0.9 or less, preferably 1:0.8 or less, more preferably 1:0.7 or less, still more preferably 1:0.65 or less, most preferably 1:0.5 or less. The lower the upper limit value, the less heterodimer is formed under conditions in which cells expressing the first antigen and the second antigen are not present, and side effects are further reduced.

On the other hand, as the lower limit value of the binding amount of the second antigen-binding molecule, the molar ratio may be 1:0.1 or more, preferably 1:0.14 or more, more preferably 1:0.17 or more, still more preferably 1:0.2 or more, and most preferably 1:0.23 or more. The higher the lower limit value, the more easily heterodimers of the first antigen-binding molecule and the second antigen-binding molecule are formed on the surface of cells expressing the first antigen and the second antigen, and the effector function becomes higher.

Examples of a surface plasmon resonance apparatus include Biacore (registered trademark) T200 (GE Healthcare).

Examples of a measurement solution used for surface plasmon resonance measurement include HBS-EP+10X (GE Healthcare). Since HBS-EP+10X is a measurement solution concentrated 10 times, it is diluted to 1/10th when used. The specific composition of the measurement solution at the time of use is 0.01 M HEPES, 0.15 M NaCl, 3 mM EDTA, 0.05% (v/v) Surfactant P20, pH 7.4. The preferred temperature of the measurement solution at the time of measurement is 25° C.

In one embodiment, the first antigen-binding molecule and the second antigen-binding molecule are more likely to form heterodimers than homodimers when mixed in solution. The "homodimer" in this embodiment means a dimer formed by a noncovalent interaction between a first antigen-binding molecule and a first antigen-binding molecule or a dimer formed by a noncovalent interaction between a second antigen-binding molecule and a second antigen-binding molecule. Moreover, the "heterodimer" is a dimer formed by a noncovalent interaction between a first antigen-binding molecule and a second antigen-binding molecule. Examples of the interactions include hydrogen bonding and intermolecular bonding.

From the viewpoint of reducing side effects, the first antigen-binding molecule and the second antigen-binding molecule are preferably less likely to interact in solution. However, since the interaction between the first antigen-binding molecule and the second antigen-binding molecule is in a state of equilibrium, interaction may occur when the concentration of the first antigen-binding molecule and the second antigen-binding molecule in solution is increased more than the concentration in the pharmaceutical composition suitable for administration to a subject. In that case, the higher the concentration of the first antigen-binding molecule and the second antigen-binding molecule, the greater the amount of the interacting first antigen-binding molecule and second antigen-binding molecule.

A specific embodiment of the first antigen-binding molecule and the second antigen-binding molecule which are more likely to form heterodimers than homodimers when mixed in solution includes an embodiment wherein the first polypeptide comprises a first CH3 and the second polypeptide comprises a second CH3, and wherein at least one modification of (i) to (iii) below is included as a modification to make the first CH3 and the second CH3 easier to form the heterodimer than the homodimers when mixed in solution:

(i) a modification where either one of the first CH3 and the second CH3 has a positively-charged region and the other has a negatively-charged region, and when the heterodimer is formed, the positively-charged region interacts with the negatively-charged region, (ii) a modification where either one of the first CH3 and the second CH3 has a convex portion and the other has a concave portion, and when the heterodimer is formed, the convex portion fits into and interacts with the concave portion, and (iii) a modification where the first CH3 and the second CH3 are modified IgG CH3, a part of which is replaced with a part of IgA CH3, and when said heterodimer is formed, the replaced part of IgA CH3 in said first CH3 interacts with the replaced part of IgA CH3 in said second CH3.

Examples of the modification of (i) include those disclosed in WO 2006/106905, WO 2009/089004, WO 2010/129304, and WO 2014/084607. An example of a specific method is: modifying at least one combination from among the combinations of positions 356 and 439, positions 357 and 370, and position 399 and 409 of the EU numbering system in the amino acid sequence of the heavy chain constant region of the polypeptide having the first antigen-binding activity, to amino acids having the same charge; and modifying at least one combination from among the combinations of positions 356 and 439, positions 357 and 370, and position 399 and 409 of the EU numbering system in the heavy chain constant region of the polypeptide having the second antigen-binding activity or not having antigen-binding activity, to amino acids having a charge opposite to that of the polypeptide having the first antigen-binding activity. More specifically, for example, in the amino acid sequences of the heavy chain constant regions of the polypeptide having the first antigen-binding activity and the polypeptide having the second antigen-binding activity, either one of the polypeptides is introduced with a mutation that substitutes Glu at position 356 in the EU numbering system with Lys, and the other polypeptide is introduced with a mutation that substitutes Lys at position 439 in the EU numbering system with Glu.

Examples of the modification of (ii) include those disclosed in WO 96/027011 and Margaret Merchant et al., Nature Biotechnology 1998, 16, 677-681. Examples of specific methods are: the combination of introducing T366Y to one CH3 and Y407A to the other CH3; or the combination of introducing T366W to one CH3 and Y407A to the other CH3, or the combination of introducing F405A to one CH3 and T394W to the other CH3, or the combination of introducing Y407T to one CH3 and T366Y to the other CH3, or the combination of introducing T366Y/F405A to one CH3 and T394W/Y407T to the other CH3, or the combination of introducing T366W/F405W to one CH3 and T394S/Y407A to the other CH3, or the combination of introducing F405W/Y407A to one CH3 and T366W/T394S to the other CH3, or the combination of introducing F405W to one CH3 and T394S to the other CH3, or the combination of introducing T366W to one CH3 and T366S/L368A/Y407V to the other CH3. The modification of (ii) can be combined with the modification of (i). Examples of such combinations include those disclosed in WO 2012/058768.

The modification of (iii) is a technique of using strand-exchange engineered domain CH3s, in which a part of one H chain CH3 of an antibody is modified to a sequence derived from IgA corresponding to that part, and the complementary part of the other H chain CH3 is introduced with an IgA-derived sequence corresponding to that part, to efficiently induce the interaction of polypeptides having different sequences by complementary interaction of the CH3s (Protein Engineering Design & Selection, 23; 195-202, 2010). This known technique can also be used to make it easier to form a heterodimer efficiently. Examples of the modification of (iii) include the modification technique disclosed in WO 2007/110205.

As another specific embodiment of the first antigen-binding molecule and the second antigen-binding molecule which are more likely to form heterodimers than homodimers when mixed in solution, modifications added to the hinge region portion may be applied. Such modifications include, for example, the modification technique disclosed in WO 2011/143545.

Either or both of the first CH3 and the second CH3 preferably has a substitution of at least one of the amino acid residues at positions 357, 397, and 409 in the EU numbering system to another amino acid residue. By adding such a modification, it becomes possible to set the binding amount of the second antigen-binding molecule to the first antigen-binding molecule easily within the range of the above-mentioned molar ratio when affinity between the two antigen-binding molecules is measured using a sensor chip on which 50 pg of the first antigen-binding molecule is immobilized per 1 $mm^2$ and a measurement solution containing 2.5 mg/mL of the second antigen-binding molecule in the surface plasmon resonance described above.

In one embodiment, it is preferred that the amount of heterodimer formation under conditions in which cells expressing the first antigen and the second antigen are present is greater than that under conditions in which the cells are not present.

Conditions in which said cells are not present encompass conditions in which cells expressing the first antigen and the second antigen are not present but there are cells expressing the first antigen without expressing the second antigen or cells expressing the second antigen without expressing the first antigen. That is, "the amount of heterodimer formation under conditions in which cells expressing the first antigen and the second antigen are present is greater than that under conditions in which the cells are not present" encompasses a case in which the amount of heterodimer formation on the surface of cells expressing the first antigen and the second antigen is greater than the amount of heterodimer formation on the surface of cells expressing the first antigen without expressing the second antigen or cells expressing the second antigen without expressing the first antigen, when the pharmaceutical composition is administered to a living body.

In one embodiment, when the heterodimer is formed on the surface of cells expressing the first antigen and the second antigen, the binding activity of the heterodimer to FcγR is higher than the binding activity of the monomer of the first antigen-binding molecule or the monomer of the second antigen-binding molecule to FcγR, or, when the homodimers are formed, than the binding activity of the homodimers to FcγR. This means, for example, that when the pharmaceutical composition is administered to a subject having cells expressing the first antigen and the second antigen, the heterodimer formed by the first antigen-binding molecule and the second antigen-binding molecule that have reached the cell surface leads to greater activation of FcγR than the monomers simply bound to the cell surface or the homodimers formed on the cell surface, and exerts an effector function. This further reduces side effects.

In this embodiment, the FcγR includes, for example, rodent and primate FcγRs and may be any one of these FcγRs. In this embodiment, the FcγR is preferably a rodent and a primate FcγR. Rodents are preferably mice and rats. Primates are preferably cynomolgus monkeys and humans. In this embodiment, the FcγR includes human FcγRs, and rodent and nonhuman primate homologs that are structurally homologous and functionally similar to human FcγRs.

Subclasses of FcγR in this embodiment include human FcγRI, human FcγRII, and human FcγRIII, and rodent and non-human primate homologs thereof. Among these, FcγR is preferably a human FcγRII or human FcγRIII, or a rodent and nonhuman primate homolog thereof, more preferably, human FcγRIII or a rodent and nonhuman primate homolog thereof. The human FcγR is preferably human FcγRII or human FcγRIII, more preferably human FcγRIII.

Human FcγRII in this embodiment is further divided into human FcγRIIA, human FcγRIIB, and human FcγRIIC. Among these, human FcγRII is preferably human FcγRIIB. Human FcγRIII is further divided into human FcγRIIIA and human FcγRIIIB. Among these, human FcγRIII is preferably human FcγRIIIA.

In one embodiment, the effector function under conditions in which cells expressing the first antigen and the second antigen are present is higher than that under conditions in which cells expressing the first antigen without expressing the second antigen or cells expressing the second antigen without expressing the first antigen are present. This further reduces side effects.

The effector function is preferably ADCC and CDC, more preferably ADCC.

In one embodiment, when either or both of the first polypeptide and the second polypeptide comprise a hinge region portion in the antibody-half molecule, the hinge region portion in either or both of the first polypeptide and the second polypeptide has a substitution of a cysteine residue with another amino acid residue at either or both of positions 226 and 229 in the EU numbering system. In this embodiment, preferably, the hinge region portion in both the first polypeptide and the second polypeptide has a substitution of a cysteine residue with another amino acid residue at either or both of positions 226 and 229 in the EU numbering system, or the hinge region portion in either or both of the first polypeptide and the second polypeptide has a substitution of a cysteine residue with another amino acid residue at both positions 226 and 229 in the EU numbering system. More preferably, the hinge region portion in both the first polypeptide and the second polypeptide has a substitution of a cysteine residue with another amino acid at both positions 226 and 229 in the EU numbering system. This substitution can suppress disulfide bonds between H chains, making the first antigen-binding molecule and the second antigen-binding molecule more likely to be not linked by covalent bonds.

In this embodiment, it is more preferable that the substitution of a cysteine residue with another amino acid residue at either or both of positions 226 and 229 in the EU numbering system is combined with the above mentioned substitution of at least one of amino acid residues at positions 357, 397 and 409 in the EU numbering system with another amino acid residue in either or both the first CH3 and the second CH3. As a result of this combination of modifications, the first antigen-binding molecule and the second antigen-binding molecule are not covalently linked, and further, when mixed in solution, they are more likely to form the heterodimer than the homodimers.

4. Other Components

The pharmaceutical compositions may contain other components besides the first antigen-binding molecule and the second antigen-binding molecule.

Examples of other components include pharmaceutically acceptable carriers.

The pharmaceutical compositions can be formulated by methods known to those skilled in the art. For example, such pharmaceutical compositions can be used parenterally, as injections which are sterile solutions or suspensions including an antibody along with water or another pharmaceutically acceptable liquid. For example, such compositions may be formulated as unit doses that meet the requirements for the preparation of pharmaceuticals by appropriately combining the antibody with pharmaceutically acceptable carriers or media, specifically with sterile water, physiological saline, a vegetable oil, emulsifier, suspension, detergent, stabilizer, flavoring agent, excipient, vehicle, preservative, binder, or such. In such preparations, the amount of active ingredient is adjusted such that the dose falls within an appropriately pre-determined range.

Sterile compositions for injection can be formulated using vehicles such as distilled water for injection, according to standard protocols for formulation.

Aqueous solutions for injection include, for example, physiological saline and isotonic solutions containing dextrose or other adjuvants (for example, D-sorbitol, D-mannose, D-mannitol, and sodium chloride). Appropriate solubilizers, for example, alcohols (ethanol and such), polyalcohols (propylene glycol, polyethylene glycol, and such), non-ionic detergents (polysorbate 80™, HCO-50, and such), may be used in combination.

Oils include sesame and soybean oils. Benzyl benzoate and/or benzyl alcohol can be used in combination as solubilizers. Buffers (for example, phosphate buffer and sodium acetate buffer), soothing agents (for example, procaine hydrochloride), stabilizers (for example, benzyl alcohol and phenol), and/or antioxidants can also be combined. Prepared injectables are generally filled into appropriate ampules.

In one embodiment, when the target disease of the pharmaceutical composition is a malignant tumor among cell proliferative diseases, both the first antigen and the second antigen are preferably cancer antigens, and the pharmaceutical composition contains a cytotoxic agent as another component. The cytotoxic agent includes immunity checkpoint inhibitors in addition to those exemplified above.

5. Dosage Form

The pharmaceutical compositions are preferably administered parenterally. For example, the compositions may be injections, transnasal compositions, transpulmonary compositions or transdermal compositions. For example, such compositions can be administered systemically or locally by intravenous injection, intramuscular injection, intraperitoneal injection, subcutaneous injection, or such.

The first antigen-binding molecule and the second antigen-binding molecule may be formulated into the same agent or may be formulated into separate agents. When the pharmaceutical compositions contain a cytotoxic agent as another component, the cytotoxic agent may be formulated into the same agent as, or into an agent separate from, the first antigen-binding molecule or the second antigen-binding molecule. When formulated into separate agents, the timing of administration can be determined for each contained component.

6. Target Disease

The target disease of the pharmaceutical compositions is not particularly limited, but is preferably a disease caused by a pathogenic cell expressing the first antigen and the second antigen. That is, the disease is a disease in which it is desirable that the first antigen-binding molecule and the second antigen-binding molecule form a heterodimer on the cell surface and exert effector function.

Specific target diseases include, for example, cell proliferative diseases, hyperimmune diseases, and infectious diseases. Cell proliferative diseases include tumors. Examples of the hyperimmune diseases include autoimmune diseases. Infectious diseases include bacterial and viral infections.

7. Production Method

The first antigen-binding molecule and the second antigen-binding molecule are produced by a general method for obtaining a protein. Antigen-binding molecules are generally obtained by expressing them in host cells using nucleic acids encoding them. The antigen-binding molecule expressed in the host cell is usually recovered from the host cell and purified. The first antigen-binding molecule and the second antigen-binding molecule may be obtained by co-expression in a host cell or may be obtained by expression in separate host cells. A specific production method is described below.

The nucleic acids are ordinarily carried by (inserted into) suitable vectors and then introduced into host cells. These vectors are not particularly limited so long as the inserted nucleic acid is stably maintained. For example, when using *E. coli* as the host, the cloning vector is preferably a pBluescript vector (Stratagene) and such, but various commercially available vectors may be used. Expression vectors are particularly useful as vectors for producing the antigen-binding molecules. Expression vectors are not particularly limited so long as they can express polypeptides in test tubes, *E. coli*, cultured cells, or individual organisms. For example, preferred vectors include pBEST vector (Promega) for expression in test tubes, pET vector (Invitrogen) for *E. coli*, pME18S-FL3 vector (GenBank Accession No. AB009864) for cultured cells, and pME18S vector (Mol. Cell Biol. 8:466-472(1998)) for individual organisms. Insertion of a DNA of the present invention into vectors can be performed by standard methods such as ligase reactions using restriction enzyme sites (Current protocols in Molecular Biology edit. Ausubel et al. (1987) Publish. John Wiley & Sons. Section 11.4-11.11).

The above-mentioned host cells are not particularly limited, and various host cells can be used, depending on the purpose. Cells used for expressing the antigen-binding molecules include bacterial cells (for example, *Streptococcus, Staphylococcus, E. coli, Streptomyces*, and *Bacillus subtilis*), fungal cells (for example, yeast and *Aspergillus*), insect cells (for example, *Drosophila* S2 and *Spodoptera* SF9), animal cells (for example, CHO, COS, HeLa, C127, 3T3, BHK, HEK293, Bowes melanoma cell), and plant cells. Vectors can be introduced into host cells using known methods, such as the calcium phosphate precipitation method, electroporation method (Current protocols in Molecular Biology edit. Ausubel et al. (1987) Publish. John Wiley & Sons. Section 9.1-9.9), lipofectamine method (GIBCOBRL), and microinjection method.

For secreting host cell-expressed antigen-binding molecules into the lumen of the endoplasmic reticulum, periplasmic space, or extracellular environment, suitable secretion signals can be incorporated into the antigen-binding molecules of interest. These signals may be intrinsic or foreign to the antigen-binding molecules of interest.

When the antigen-binding molecules of the present invention are secreted into the culture media, the antigen-binding molecules produced by the above-mentioned method can be harvested by collecting the media. When the antigen-binding molecules of the present invention are produced inside cells, first, the cells are lysed, and then these antigen-binding molecules are collected.

The antigen-binding molecules of the present invention can be collected and purified from recombinant cell cultures by using known methods, including ammonium sulfate or ethanol precipitation, acidic extraction, anion or cation exchange chromatography, phosphocellulose chromatography, hydrophobic interaction chromatography, affinity chromatography, hydroxyapatite chromatography, and lectin chromatography.

In the preparation of bispecific antibodies in which the H chains are linked by covalent bonds such as disulfide bonds, purification steps are often required to eliminate antigen-binding molecules in which undesired H chain and L chain are combined. On the other hand, in the production of the first antigen-binding molecule and the second antigen-binding molecule of the present invention, since the first antigen-binding molecule and the second antigen-binding molecule are not covalently bound to each other, such purification steps can be omitted. For example, when the first antigen-binding molecule and the second antigen-binding molecule are co-expressed in a host cell, one only has to collect the fractions that contain the first antigen-binding molecule and the second antigen-binding molecule from the medium or cell lysate by various kinds of chromatographies. When the first antigen-binding molecule and the second antigen-binding molecule are expressed in separate host cells, the antigen-binding molecules may be purified after mixing the medium or cell lysate, or the first antigen-binding molecule and the second antigen-binding molecule may be separately purified from the medium or cell lysate and then mixed. From the viewpoint of reducing the labor of the purification step to eliminate antigen-binding molecules in which undesired H chain and L chain are combined and reducing wastage of the antigen-binding molecules eliminated in this step, the first antigen-binding molecule and the second antigen-binding molecule are preferably expressed in separate host cells.

When mixing and preparing a first antigen-binding molecule and a second antigen-binding molecule just prior to administering a pharmaceutical composition to a subject, or when sequentially administering the later-described first pharmaceutical composition that contains a first antigen-binding molecule but does not contain a second antigen-binding molecule, and a third pharmaceutical composition that contains a second antigen-binding molecule but does not contain a first antigen-binding molecule, preferably, the first antigen-binding molecule and the second antigen-binding molecule are expressed in separate cells and purified to produce pharmaceutical compositions separately containing the first antigen-binding molecule and the second antigen-binding molecule.

C. Other Embodiments of Antigen-Binding Molecules and Pharmaceutical Compositions 1. Another Embodiment of the First Antigen-Binding Molecule Another specific embodiment of the first antigen-binding molecule includes, for example, a first antigen-binding molecule having a first antigen-binding region that binds to a first antigen, and a first polypeptide that includes either or both of a first CH2 and a first CH3, wherein said first antigen-binding molecule, when mixed in solution with a second antigen-binding molecule having a second antigen binding region that binds to a second antigen, and a second polypeptide comprising either or both of a second CH2 and a second CH3, is more likely to form a heterodimer with the second antigen binding molecule than a homodimer between the first antigen binding molecules, and in the heterodimer, the first antigen-binding molecule and the second antigen-binding molecule are not linked by a covalent bond.

In this embodiment, the first antigen-binding region, the first polypeptide, and parts other than these are the same as those described in "1. First antigen-binding molecule". The second antigen-binding region, the second polypeptide, and parts other than these are the same as those described in "2. Second antigen-binding molecule". The relationship between the first antigen-binding molecule and the second antigen-binding molecule is the same as that described in "3. Relationship between first antigen-binding molecule and second antigen-binding molecule".

The first antigen-binding molecule in this embodiment can be prepared as a first pharmaceutical composition containing it, but not containing the second antigen-binding molecule. In this case, a second pharmaceutical composition containing the second antigen-binding molecule is prepared separately. The second pharmaceutical composition may or may not contain the first antigen-binding molecule. The second pharmaceutical composition may or may not be produced within the same establishment. The first pharmaceutical composition and the second pharmaceutical composition are used in combination for a subject.

In this embodiment, the first pharmaceutical composition is the same as in the above-mentioned "1. First antigen-binding molecule", "2. Second antigen-binding molecule", "3. Relationship between first antigen-binding molecule and second antigen-binding molecule", "4. Other components", "5. Dosage form", "6. Target diseases" and "7. Production Method", with the exception that it does not contain the second antigen-binding molecule.

2. Another Embodiment of the Second Antigen-Binding Molecule

Another specific embodiment of the second antigen-binding molecule includes, for example, a second dantigen-binding molecule having a second antigen-binding region that binds to a second antigen, an a second polypeptide that comprise either or both of a second CH2 and a second CH3, wherein said second antigen-binding molecule, when mixed in solution with a first antigen binding molecule having a first antigen binding region that binds to a first antigen, and a first polypeptide comprising either or both of a first CH2 and a first CH3, is more likely to form a heterodimer with the first antigen-binding molecule than a homodimer between the second antigen-binding molecules, and in the heterodimer, the second antigen-binding molecule and the first antigen-binding molecule are not linked by a covalent bond.

In this embodiment, the first antigen-binding region, the first polypeptide, and parts other than these are the same as those described in "1. First antigen-binding molecule". The second antigen-binding region, the second polypeptide, and parts other than these are the same as those described in "2. Second antigen-binding molecule". The relationship between the first antigen-binding molecule and the second antigen-binding molecule is the same as that described in "3. Relationship between first antigen-binding molecule and second antigen-binding molecule".

The second antigen-binding molecule in this embodiment can be prepared as a third pharmaceutical composition containing it, but not containing the first antigen-binding molecule. In this case, a fourth pharmaceutical composition containing the first antigen-binding molecule is prepared separately. The fourth pharmaceutical composition may or may not contain the first antigen-binding molecule. The third pharmaceutical composition and the fourth pharmaceutical composition are used in combination.

In this embodiment, the third pharmaceutical composition is the same as in the above-mentioned "1. First antigen-binding molecule", "2. Second antigen-binding molecule", "3. Relationship between first antigen-binding molecule and second antigen-binding molecule", "4. Other components", "5. Dosage form", "6. Target diseases" and "7. Production Method", with the exception that it does not contain the first antigen-binding molecule.

3. Another Embodiment of the Pharmaceutical Compositions

Another specific embodiment of the pharmaceutical compositions includes, for example, a pharmaceutical composition which contains a first antigen-binding molecule having a first antigen-binding region that binds to a first antigen and a first polypeptide comprising a first CH3, and a second antigen-binding molecule having a second antigen-binding region that binds to a second antigen and a second polypeptide comprising a second CH3, and wherein said first antigen-binding molecule and said second antigen-binding molecule are not linked by a covalent bond, and wherein said first CH3 and said second CH3 have at least one modification of (iv) to (vi) below:

(iv) a modification where either one of the first CH3 and the second CH3 has a positively-charged region, and the other has a negatively-charged region, and when the heterodimer is formed, the positively-charged region interacts with the negatively-charged region, (v) a modification where either one of the first CH3 and the second CH3 has a convex portion and the other has a concave portion, and when the heterodimer is formed, the convex portion fits into and interacts with the concave portion, and (vi) a modification where the first CH3 and the second CH3 are modified IgG CH3 a part of which is replaced with a part of IgA CH3, and when said heterodimer is formed, the replaced part of IgA CH3 in said first CH3 interacts with the replaced part of IgA CH3 in said second CH3.

In this embodiment, the first antigen-binding molecule and the second antigen-binding molecule are the same as in the above-described "1. First antigen-binding molecule" and "2. Second antigen-binding molecule". Details of the pharmaceutical composition of this embodiment are the same as in the above-described "4. Other components", "5. Dosage form", "6. Target diseases" and "7. Production method".

Examples of the modifications of (iv) include those disclosed in WO 2006/106905, WO 2009/089004, WO 2010/129304, and WO 2014/084607. An example of a specific method is: modifying at least one combination from among the combinations of positions 356 and 439, positions 357 and 370, and position 399 and 409 according to the EU numbering system in the amino acid sequence of the heavy chain constant region of the polypeptide having the first antigen-binding activity, to amino acids having the same charge; and modifying at least one combination from among the combinations of positions 356 and 439, positions 357 and 370, and positions 399 and 409 according to the EU numbering system in the heavy chain constant region of the polypeptide having the second antigen-binding activity or not having antigen-binding activity, to amino acids having a charge opposite to that of the polypeptide having the first antigen-binding activity. More specifically, for example, in the amino acid sequences of the heavy chain constant regions of the polypeptide having the first antigen-binding activity and the polypeptide having the second antigen-binding activity, either one of the polypeptides is introduced with a mutation that substitutes Glu at position 356 in the EU numbering system with Lys, and the other polypeptide is introduced with a mutation that substitutes Lys at position 439 in the EU numbering system with Glu.

Examples of the modification of (v) include those disclosed in WO 96/027011 and Margaret Merchant et al., Nature Biotechnology 1998, 16, 677-681. Examples of specific methods are: the combination of introducing T366Y to one CH3 and Y407A to the other CH3; or the combination of introducing T366W to one CH3 and Y407A to the other CH3, or the combination of introducing F405A to one CH3 and T394W to the other CH3, or the combination of introducing Y407T to one CH3 and T366Y to the other CH3, or the combination of introducing T366Y/F405A to one CH3 and T394W/Y407T to the other CH3, or the combination of introducing T366W/F405W to one CH3 and T394S/Y407A to the other CH3, or the combination of introducing F405W/Y407A to one CH3 and T366W/T394S to the other CH3, or the combination of introducing F405W to one CH3 and T394S to the other CH3, or the combination of introducing T366W to one CH3 and T366S/L368A/Y407V to the other CH3. The modification of (v) can be combined with the modification of (iv). Examples of such combinations include those disclosed in WO 2012/058768.

The modification of (vi) is a technique of using strand-exchange engineered domain CH3s, in which a part of one H chain CH3 of an antibody is modified to a sequence derived from IgA corresponding to that part, and the complementary part of the other H chain CH3 is introduced with an IgA-derived sequence corresponding to that part, to efficiently induce the interaction of polypeptides having different sequences by complementary interaction of the CH3s (Protein Engineering Design & Selection, 23; 195-202, 2010). This known technique can also be used to make it easier to form a heterodimer efficiently. Examples of the modification of (vi) include the modification technique disclosed in WO 2007/110205.

As another specific embodiment of the first antigen-binding molecule and the second antigen-binding molecule which are more likely to form heterodimers than homodimers when mixed in solution, modifications added to the hinge region portion may be applied. Such modifications include, for example, the modification technique disclosed in WO 2011/143545.

Either or both of the first CH3 and the second CH3 preferably has a substitution of at least one of the amino acid residues at positions 357, 397, and 409 in the EU numbering system with another amino acid residue. By adding such a modification, it becomes possible to set the binding amount of the second antigen-binding molecule to the first antigen-binding molecule easily within the range of the above mentioned-molar ratio when affinity between the two antigen-binding molecules is measured using a sensor chip on which 50 pg of the first antigen-binding molecule is immobilized per 1 $mm^2$ and a measurement solution containing 2.5 mg/ml of the second antigen-binding molecule in the surface plasmon resonance described above.

D. Method of Treatment

In one aspect, the present invention provides a method of treatment comprising simultaneous or sequential administration of a first antigen-binding molecule and a second antigen-binding molecule to a subject. Subjects suitable for the method of treatment have a disease caused by a pathogenic cell expressing the first antigen and the second antigen.

The first antigen-binding molecule is the same as that in the above-mentioned "1. First antigen-binding molecule" of "B. Pharmaceutical compositions", or "1. Another embodiment of the first antigen-binding molecule" in "C. Other embodiments of antigen-binding molecules and pharmaceutical compositions".

The second antigen-binding molecule is the same as that in the above-mentioned "2. Second antigen-binding molecule" of "B. Pharmaceutical compositions", or "2. Another embodiment of the second antigen-binding molecule" of "C. Other embodiments of antigen-binding molecules and pharmaceutical composition".

The first antigen-binding molecule and the second antigen-binding molecule are not linked by a covalent bond before and after administration, but exert effector function by forming the heterodimer of the first antigen-binding molecule and the second antigen-binding molecule on the surface of the pathogenic cell.

Simultaneous administration encompasses administration of a pharmaceutical composition containing a first antigen-binding molecule and a second antigen-binding molecule, as well as simultaneous administration of a first pharmaceutical composition containing a first antigen-binding molecule but not a second antigen-binding molecule and a third pharmaceutical composition containing a second antigen-binding molecule but not a first antigen-binding molecule.

In sequential administration, the first pharmaceutical composition containing a first antigen-binding molecule but not a second antigen-binding molecule, and the third pharmaceutical composition containing a second antigen-binding molecule but not a first antigen-binding molecule are administered with an interval between each other. The administration interval of the first pharmaceutical composition and the second pharmaceutical composition is set within such a range that after administration, the first antigen-binding molecule and the second antigen-binding molecule form a heterodimer on the surface of the pathogenic cell, to exert effector function.

"Simultaneous or sequential administration" encompasses a combination of simultaneous administration and sequential administration.

The administration methods can be appropriately selected in consideration of a patient's age and symptoms. The dose of a pharmaceutical composition composed of an antibody or a polynucleotide encoding an antibody may be, for example, from 0.0001 to 1000 mg/kg for each administration. Alternatively, the dose may be, for example, from 0.001 to 100,000 mg per patient. However, the doses are not limited to the ranges described above. The doses and administration methods vary depending on a patient's weight, age, symptoms, and such. Those skilled in the art can select appropriate doses and administration methods in consideration of the factors described above.

E. Screening Method

In one aspect, the present invention provides a method of screening for selecting a combination of a first antigen-binding molecule and a second antigen-binding molecule. The screening method is a method of selecting a combination of a first antigen-binding molecule and a second antigen-binding molecule.

The combination is selected from a group of variants of the first antigen-binding molecule and a group of variants of the second antigen-binding molecule.

The group of variants of the first antigen-binding molecule is a group of antigen-binding molecule variants that have a first antigen-binding region which binds to a first antigen and a first polypeptide comprising either or both of a first CH2 and a first CH3.

The group of variants of the twenty-first antigen-binding molecule is a group of antigen-binding molecule variants that have a second antigen-binding region which binds to a second antigen and a second polypeptide comprising either or both of a second CH2 and a second CH3.

The combination of the first antigen-binding molecule and the second antigen-binding molecule is selected from these groups as a combination which satisfies all of the following (a) to (c):

(a) the first antigen-binding molecule and the second antigen-binding molecule are not linked by a covalent bond, (b) the first antigen-binding molecule and the second antigen-binding molecule are more likely to form heterodimers between the first antigen-binding molecule and the second antigen-binding molecule than homodimers of the first antigen-binding molecules or homodimers of the second antigen-binding molecules, and (c) a sensor chip on which 50 pg per $mm^2$ of the first antigen-binding molecule is immobilized and a measurement solution containing 2.5 mg/mL of the second antigen-binding molecule are used in surface plasmon resonance to measure affinity between the two antigen-binding molecules, the binding amount of the second antigen-binding molecule to the first antigen-binding molecule is within the range of 1:0.1 to 1:0.9 in terms of molar ratio.

As a selection method for (a) and (b), for example, a method of fractionation based on molecular size is adopted. Specific methods include size exclusion chromatography.

The selection method for (c) is carried out, for example, depending on whether or not the molar ratio calculated from the result using surface plasmon resonance is within the above range.

EXAMPLES

Test Example 1

Preparation of Expression Vectors for Antibody-Half Molecules and Expression and Purification of Antibody-Half Molecules Introduction of amino acid substitution was carried out by a method known to those skilled in the art using QuikChange Site-Directed Mutagenesis Kit (Stratagene), PCR or In-fusion Advantage PCR cloning kit (TAKARA) and the like, to construct expression vectors. The nucleotide sequences of the obtained expression vectors were determined by a method known to those skilled in the art. The prepared plasmids were transiently introduced into human embryonic kidney cancer cell-derived HEK293H strain (Invitrogen) or FreeStyle293 cells (Invitrogen) to express antibody-half molecules. The antibody-half molecules were purified from the obtained culture supernatant by a method known to those skilled in the art using rProtein A Sepharose (registered trademark) Fast Flow (GE Healthcare). Purified antibody-half molecule concentration was calculated by measuring the absorbance at 280 nm using a spectrophotometer and calculating the antibody-half molecule concentration from the obtained value using the extinction coefficient calculated by the PACE method (Protein Science 1995; 4: 2411-2423).

Test Example 2

Analysis of the Molecular Weight of Antibody-Half Molecules

The molecular weight of the obtained antibody-half molecules was analyzed by a method known to those skilled in the art using HPLC, Agilent 1260 Infinity (registered trademark) (Agilent Technologies), and using a G3000SW$_{XL}$ column (TOSOH). The protein concentration of the antibody-half molecules was 0.25 mg/mL, and 80 μL was injected.

Test Example 3

Preparation of FcγR and Evaluation of Binding Activity to FcγR

The extracellular domain of FcγR was prepared by the following method. First, the gene of the extracellular domain of FcγR was synthesized by a method known to those skilled in the art. At this time, as polymorphisms are known for FcγRIIIa, polymorphic sites were prepared referring to J. Clin. Invest. 1997, 100 (5): 1059-1070.

The obtained gene fragment was inserted into an animal cell expression vector to prepare an expression vector. The prepared expression vector was transiently introduced into FreeStyle293 cells derived from human embryonic kidney cancer cells (Invitrogen) to express the protein of interest. After culturing, the obtained culture supernatant was recovered, and passed through a 0.22 μm filter to obtain the culture supernatant. Basically, the obtained culture supernatant was purified in the following 4 steps. The first step was cation exchange column chromatography (SP Sepharose (registered trademark) FF), the second step was affinity column chromatography to His tag (HisTrap HP), the third step was gel filtration column chromatography (Superdex (registered trademark) 200), and the fourth step was aseptic filtration. The absorbance at 280 nm was measured for the purified protein using a spectrophotometer and the concentration of the purified protein was calculated from the obtained value by using the extinction coefficient calculated by PACE or the like (Protein Science 1995; 4: 2411-2423).

Interaction analysis of antibody-half molecules of interest and FcγR was performed using Biacore (registered trademark) T200. Biotin CAPture Kit, Series S (GE Healthcare) was used for the measurement, and HBS-EP+10X (GE Healthcare) diluted 1/10th was used as a running buffer. The measurement temperature was 25° C. For the sensor chip, Series S Sensor Chip CAP (GE Healthcare) onto which previously-biotinylated antigen peptides were allowed to interact and thereby immobilized was used. These chips were allowed to capture the antibody-half molecules of interest and then interact with FcγR diluted with the running buffer. The antigens and antibody-half molecules captured on the chip were washed as described in the instructions attached to the kit, and the chips were regenerated and reused.

The binding activity of antibody-half molecules to FcγR was evaluated mainly based on the binding activity to FcγR and the dissociation constant for FcγR as indicators.

The dissociation constant of each antibody-half molecule for FcγR was calculated by performing kinetic analysis of the measurement result of Biacore (registered trademark). Specifically, the sensorgram obtained by the measurement was subjected to global fitting with a 1:1 Langmuir binding model using Biacore (registered trademark) Evaluation Software to calculate the association rate constant ka (L/mol/s) and the dissociation rate constant kd (1/s), and the dissociation constant KD (mol/L) was calculated from those values.

Test Example 4

Measurement of ADCC Activity of Each Test Antibody-Half Molecule Using FcγRIIIa-V158 Jurkat Cells (Promega) as Effector Cells ADCC activity of each test antibody-half molecule was measured as follows using FcγRIIIa-V158 Jurkat cells (hereinafter referred to as Jurkat cells) as effector cells.

Preparation of Jurkat Cells

Jurkat cells were recovered from a flask and washed once with RPMI 1640 medium (Gibco) containing 4% FBS (hereinafter referred to as "assay buffer"), and then the cells were suspended in the assay buffer at a cell density of $3\times10^6$ cells/mL. The cell suspension was used as a Jurkat cell solution for subsequent experiments.

(1) Preparation of Target Cells

SK-pca60, SKE-4B2, or EREG_SK-pca60_#2, which is SK-Hep-1 forced to express human glypican 3, human epiregulin, or both human glypican 3 and human epiregulin, respectively, was detached from dishes, washed once with the assay buffer, and then suspended in the assay buffer to a cell density of $1\times10^6$ cells/mL. The cell suspensions were used as target cell solutions for subsequent experiments.

(2) Preparation of Luminescent Reagent 100 mL of Bio-Glo Luciferase Assay buffer (Promega) was added to a Bio-Glo Luciferase Assay Substrate (Promega) bottle and mixed by inverting. This bottle was shielded from light and frozen at −20° C. This luminescent reagent was used for subsequent experiments.

(3) ADCC Reporter Test (ADCC Activity)

ADCC activity was evaluated by fold change of luciferase luminescence. First, 25 μl ($2.5\times10^4$ cells/well) of the target cells prepared in (2) was added to each well of a 96-well flat bottom white plate. Next, 25 μl of antibody-half molecule solutions adjusted to each concentration (0.00003, 0.0003, 0.003, 0.03, 0.3, 3, and 30 μg/mL) was added into each well. To each well was added 25 μl ($7.5\times10^4$ cells/well) of each of the Jurkat cell solution prepared in (1), and the plate was left to stand at 37° ° C. for 24 hours in a 5% carbon dioxide incubator. The luminescent reagent prepared in (3) was thawed, 75 μl was added to each well, and the mixture was allowed to stand at room temperature for 10 minutes. The luciferase luminescence of 150 μl culture supernatant in each well of the plate was measured using a luminometer. ADCC activity was determined based on the following Formula 1.

$$\text{Fold change}=A/B \qquad \text{(Formula 1)}$$

In the above Formula 1, A represents the average value of luciferase luminescence of 150 μl of culture supernatant in each well. B represents the average value of luciferase luminescence of 150 μl of the culture supernatant when 25 μl of the assay buffer was added instead of the antibody-half molecule solutions in the experiment of (3). The test was carried out in triplicates, and the average value of ADCC activity (fold change) in the above test was calculated, which reflects the ADCC activity of each test antibody-half molecule.

Test Example 5

Measurement of the Interaction Between Antibody-Half Molecules

The interaction between the obtained antibody-half molecules was analyzed using Biacore (registered trademark) T200. Biotin CAPture Kit, Series S (GE Healthcare) was used for the measurement, and HBS-EP+10X (GE Healthcare) diluted 1/10th was used as a running buffer. The measurement temperature was 25° C. For the sensor chip, Series S Sensor Chip CAP (GE Healthcare) onto which previously-biotinylated antigen peptides were allowed to interact and thereby immobilized was used. These chips were allowed to capture approximately 50 RU of the antibody-half molecule A of interest and then interact with the antibody-half molecule B of interest diluted with the running buffer at 2.5 mg/mL for 180 seconds at a flow rate of 30 μL/min, and measurement was carried out. The molar binding ratio was calculated based on the following Formula 2. The antibody-half molecule A captured on the chip was washed as described in the instructions attached to the kit, and the chip was regenerated and reused.

Molar binding ratio=(binding amount of antibody-half molecule $B$ bound as analyte (RU, maximum value)/molecular weight of antibody-half molecule $B$)/(binding amount of captured antibody-half molecule $A$ (RU)/molecular weight of antibody-half molecule $A$)  (Formula 2)

Test Example 6

Measurement of blood concentration of 1D3-Kn125/H1076, 1D3-DA303v2, and 1D3-DB220v2

Measurement was done by electrochemiluminescence immunoassay (ECLIA). Plasma samples were added to a MULTI-ARRAY 96-well plate (MSD) on which Human IgG-heavy and L chain antibody (Bethyl) was immobilized, and reacted at room temperature. Subsequently, after reacting with Anti-Human IgG (Jackson Immuno Research), SULFO-TAG streptavidin (MSD) was added and reacted. Measurement was carried out with SECTOR S 600 (MSD).

Test Example 7

Measurement of Blood Concentration of 1D3-DA303v2/DB220v2

Measurement was done by LC-MS. After mixing Ab-Capcher Mag (ProteNova) and the plasma sample, a mixed solution containing lysozyme, DTT, and urea was added and reacted. Furthermore, after reacting iodoacetamide solution (Sigma Aldrich), trypsin solution was added. Thereafter, the supernatant was recovered, and trifluoroacetic acid (Wako) was added to it. This was injected into Acquity UPLC (Waters), and measured with Xevo TQ-S (Waters).

Test Example 8

Measurement of B Cells in Blood

Blood was collected from the dorsal metatarsal vein of a C57BL/6NCr S1c mouse (male, 7 weeks of age, Japan SLC Inc.) using a hemacrit capillary (Terumo Corporation). 15 μL each of the collected blood was added to 2 mL of ACK Lyncing Buffer (Gibco), incubated for 5 minutes at room temperature in the dark, and centrifuged at 500×g for 5 minutes to remove the supernatant. This was repeated. A buffer (FACS buffer) was prepared by adding 75 mL of BSA stock solution (Miltenyi Biotec) to 1450 mL of MACS buffer (Miltenyi Biotec). FcR blocking reagent (Miltenyi Biotec) was diluted 10-fold with the FACS buffer, and then the cells were suspended at 20 μL/tube. After incubation for 10 minutes at room temperature, 0.5 μL of BUV395 anti-CD45R/B220 (BD), 0.5 μL of PE-CF594 anti-IgM (BD), and 0.4 μL of Zombie NIR Fixable Viability Kit were added and incubated at 4°C for 20 minutes. Thereafter, 2 mL of FACS buffer was added, followed by centrifugation at 500×g for 5 minutes, and the supernatant was removed. The cells were resuspended in 400 μL of FACS buffer and analyzed with BD FACS LSR Fortessa X-20 (BD).

Test Example 9

Analysis of Percentage of B Cells in Viable Cells

Analysis was performed using Flowjo ver 7.6 (Tomy Digital Biology). After gating viable cells, the CD45R/B220+IgM+ fraction was defined as B cell fraction which to be analyzed. The percentage of B cells in viable cells was calculated for each sample.

Example 1

Preparation of Antibody-Half Molecules

Specific amino acid substitution procedures for preparing antibody-half molecules having double-positive cell-selective cytotoxic activity are shown below. Abbreviations and names, and CH3 modifications of prepared and evaluated antibody-half molecules, and SEQ ID NOs of the antibody-half molecules are shown in Table 1. When the name of the antibody-half molecule H chain variable region portion is VH, the sequence corresponding to the H chain of the antibody-half molecule having CH in the constant region portion is called VH-CH, and when the name of the antibody-half molecule L chain variable region portion is VL, the sequence corresponding to the L chain of the antibody-half molecule having CL in the constant region portion is called VL-CL. For example, in the case of a homodimer antibody which is expressed by using VH1-CH1 as an expression vector corresponding to the antibody-half molecule H chain and VL1-CL1 as an expression vector corresponding to the antibody-half molecule L chain, the antibody-half molecule obtained by purification after expression is denoted as VH1-CH1/VL1-CL1. When a heterodimerized antibody having four chains is expressed by using VH1-CH1 as one of the expression vectors corresponding to the antibody-half molecule H chains and VH2-CH2 for the other antibody-half molecule H chain, and using VL1-CL1 as one of the expression vectors corresponding to the antibody-half molecule L chains and VL2-CL2 for the other antibody-half molecule L chain, it is denoted as VH1-CH1/VL1-CL1//VH2-CH2/VL2-CL2. In addition, in the case of mixing the respective antibody-half molecules in equal amounts, when VH1-CH1/VL1-CL1 is used as antibody-half molecule A and VH2-CH2/VL2-CL2 is used as antibody-half molecule B, it is denoted as VH1-CH1/VL1-CL1+VH2-CH2/VL2-CL2. For the sake of simplicity, it is sometimes denoted as A1, B1, or A1+B1 using only the abbreviation of the constant region. Amino acid modifications are denoted like D356K. The first alphabet (corresponding to D of D356K) means the alphabet of the amino acid residue before modification when indicated by the one letter code, the number following it (corresponding to 356 of D356K) means the EU number of the modification position, and the last alphabet (corresponding to K of D356K) means the alphabet of the amino acid residue after modification when indicated by the one letter code. As a template to be modified, a sequence in which the terminal GK was deleted with respect to the wild-type IgG1 was used.

First, the modifications described in WO 2013/002362 were used so that ADCC activity would be enhanced upon heterodimerization. The L234Y, L235Q, G236W, S239M, H268D, D270E, and S298A substitutions and the D270E, K326D, A330M and K334E substitutions were introduced into the CH2 of antibody-half molecule A and antibody-half molecule B, respectively. In order not to form a disulfide bond between the hinge regions of the antibody, C226S and C229S were introduced into both antibody-half molecules A and B. In addition to these mutations, the modifications described in WO 2006/106905 were used as modifications to suppress the formation of homodimers and promote the formation of heterodimers. Specifically, substitutions D356K and K439E were introduced into antibody-half molecules A and B, respectively. However, since the interaction at the CH3 interface is strong, it is not possible to obtain antibody-half molecules only by these mutations. Therefore, in order to weaken the interaction at the CH3 interface, the modifications described in WO 2015/046467 were used. Modifications were introduced into both antibody-half molecules A and B at E357, V397 and K409, which are amino acid residues on CH3 interface. By combining these ADCC-enhancing modifications, hinge region modifications, heterodimerization modifications, and CH3 interface destabilization modifications, the antibody-half molecule A and antibody-half molecule B of interest were obtained. That is, homodimerization of antibody-half molecules A and antibody-half molecules B does not occur in blood or on cells on which each antigen is singly expressed, but the two antibody-half molecules heterodimerize with each other and become able to bind to FcγRIIIa only when they are simultaneously bound to cells on which the two antigens are present.

TABLE 1

| Abbreviation | Name | CH3 Modification | SEQ ID NO |
|---|---|---|---|
| A1 | MRAH-DA303v2 | D356K/V397Y/K409D | 1 |
| A2 | MRAH-DA402v2 | D356K/V397Y/K409H | 2 |
| A3 | MRAH-DA405v2 | D356K/V397Y/K409T | 3 |
| A4 | MRAH-DA424v2 | D356K/E357N/V397Y/K409D | 4 |
| A5 | MRAH-DA430v2 | D356K/E357L/V397Y/K409D | 5 |
| B1 | MRAH-DB220v2 | V397Y/K409D/K439E | 6 |
| B2 | MRAH-DB402v2 | V397Y/K409H/K439E | 7 |
| B3 | MRAH-DB405v2 | V397Y/K409T/K439E | 8 |
| B4 | MRAH-DB424v2 | E357N/V397Y/K409D/K439E | 9 |
| B5 | MRAH-DB430v2 | E357L/V397Y/K409D/K439E | 10 |

Example 2

Evaluation of Molecular Weight of Antibody-Half Molecules

Evaluation of the molecular weight of the prepared antibody-half molecules A and B was carried out by size exclusion chromatography. At this time, for the whole antibody control (peak W in FIG. 1a), the antibody against the human interleukin 6 receptor disclosed in WO 2009/125825 was used. MRAH (SEQ ID NO: 11) was used as the H chain variable region and the sequence of wild-type IgG1 (SEQ ID NO: 12) was used as the H chain constant region. MRAL (SEQ ID NO: 13) was used as the L chain variable region, and the k0 sequence (SEQ ID NO: 14), which is a wild-type κ chain was used as the L chain constant region. For the control of the half molecule state of antibody (peak H in FIG. 1b), EGLVH (SEQ ID NO: 15), which is the H chain variable region portion of the anti-human epiregulin antibody described in WO 2013/100120, was used as the H chain variable region, and wtIgG4C4 (SEQ ID NO: 16), which has the modification described by Lu et al. (Shan L, Colazet M, Rosenthal K L, Yu X Q, Bee J S, Ferguson A, Damschroder M M, Wu H, Dall'Acqua W F, Tsui P, Oganesyan V in Generation and Characterization of an IgG 4 Monomeric Fc Platform. PLOS One 2016 Aug. 1; 11 (8)), was used as the H chain constant region portion. EGLVL (SEQ ID NO: 17), which is the L chain variable region portion of the anti-human epiregulin antibody described in WO 2013/100120, was used as the L chain variable region, and the sequence of k0, which is a wild-type κ chain, was used as the L chain constant region. The assay was carried out according to the method described in Test Example 2. In this case, MRAH was used for each of the H chain variable regions, and MRAL-K0 was used for all of the L chains.

As a result of the assay, as shown in FIG. 1, in the case of antibody-half molecule A1, A3, A4, or A5 alone, a mixture of the antibody-half molecule (peak H) and the whole antibody (peak W) was obtained (FIGS. 1c and 1e to 1g). For A2, the antibody-half molecule (peak W) and a molecule (peak E) presumed to be in the state of equilibrium between antibody-half molecule and whole antibody were obtained (FIG. 1d). Antibody-half molecule B1, B2, B3, B4, or B5 alone existed as the antibody-half molecule (peak H) (FIGS. 1h to 1l). Moreover, even when antibody-half molecules A1 and B1 (FIG. 1m), A2 and B2 (FIG. 1n), A3 and B3 (FIG. 1o), A4 and B4 (FIG. 1p), A5 and B5 (FIG. 1q) were mixed, whole antibody formation (peak W) was not increased as compared to the case of antibody-half molecule A1, A2, A3, A4, or A5 alone or antibody-half molecule B1, B2, B3, B4, or B5 alone. When A1-B1 (FIG. 1m) and A3-B3 (FIG. 1o) were mixed, formation of molecules presumed to be in the state of equilibrium between antibody-half molecule and whole antibody (peak E) was observed.

Example 3

Evaluation of Binding Ability of Antibody-Half Molecules to FcγRIIIa

Next, according to the method described in Test Example 3, it was assayed whether these antibody-half molecules are in the state of antibody-half molecules in solution and do not show the ability to bind to FcγRIIIa, but heterodimerize by being locally-concentrated as a result of antigen-binding, and the binding to FcγRIIIa is restored. At this time, the assay was performed using MRAH for the H chain variable region portion, MRAL for the L chain variable region portion, and k0 for the L chain constant region portion. For the value of wild-type IgG1, the value reported by Mimoto et al. was used (Mimoto F, Igawa T, Kuramochi T, Katada H, Kadono S, Kamikawa T, Shida-Kawazoe M, Hattori K. (2013) Novel asymmetrically engineered antibody Fc variant with superior FcγR binding affinity and specificity compared with afucosylated Fc variant MAbs 5(2), 229-236).

As a result of the assay, as shown in Table 2, A1 to A5, the series of antibody-half molecules A, and B1 to B5, the series of antibody-half molecules B, did not show binding ability to FcγRIIIa when each was present alone, but showed binding ability to FcγRIIIa only when antibody-half molecules A1 and B1, A2 and B2, A3 and B3, A4 and B4, or A5 and B5 were mixed.

TABLE 2

| Constant region | KD (M)  |
|-----------------|---------|
| Wild-type IgG1  | 3.1E-07 |
| A1              | n. d.   |
| A2              | n. d.   |
| A3              | n. d.   |
| A4              | n. d.   |
| A5              | n. d.   |
| B1              | n. d.   |
| B2              | n. d.   |
| B3              | n. d.   |
| B4              | n. d.   |
| B5              | n. d.   |
| A1 + B1         | 6.1E-09 |
| A2 + B2         | 9.5E-10 |
| A3 + B3         | 1.2E-09 |
| A4 + B4         | 1.0E-08 |
| A5 + B5         | 5.3E-08 |

* n.d. stands for "not detected", meaning that measurement was not possible because the value was below the lower limit of measurement.

Example 4

Evaluation of ADCC Activity of Antibody-Half Molecules

According to the method described in Test Example 4, it was assayed whether antibody-half molecules with these constant regions have superior double-positive cell-selective cytotoxic activity relative to an existing bispecific antibody. As antigen-expressing cells, SK-pca60 and SKE-4B2 described in WO 2016/182064 and WO 2014/208482, respectively, which were obtained by forcing SK-Hep-1 to express glypican 3 and epiregulin, respectively, were used. As a glypican 3/epiregulin double-positive cell, EREG_SK-pca60_#2 obtained by forcing SK-pca60 to express epiregulin was used. At this time, for the series of antibody-half molecules A used in Example 3, those in which the H chain variable region portion is GH0 (SEQ ID NO: 18), which is of an anti-GPC3 antibody described in WO 2009/041062, the L chain variable region portion is GL0 (SEQ ID NO: 19), which is of an anti-GPC3 antibody described in WO 2009/041062, and the L chain constant region portion was k0, were used. For the antibody-half molecule B, EGLVH was used, EGLVL was used as the L chain variable region, and k0 was used as the L chain constant region. In addition, GH0-Kn125P17/GL0-k0//EGLVH-H1076N17/EGLVL-k0 (GH0/EGLVH-BiAb) was used as the existing bispecific antibody. For the constant regions of the bispecific antibody, the L234Y, L235Q, G236W, S239M, H268D, D270E, and S298A substitutions and the D270E, K326D, A330M, and K334E substitutions, as described in WO2013/002362, were introduced into the CH2 of Kn125P17 (SEQ ID NO: 20) and H1076N17 (SEQ ID NO: 21), respectively, so that the ADCC activity would be enhanced upon heterodimerization. In addition, in order to prepare the bispecific antibody utilizing the difference in electrical charge, the D356K and V397Y substitutions and the V397Y and K439E substitutions, as described in WO 2015/046467, were introduced into Kn125P17 and H1076N17, respectively. For the sequence at positions 356 to 358, the sequence of EEM, which is a wild-type IgG1 allotype, was used. The thus prepared GH0-Kn125P17/GL0-k0 and EGLVH-H1076N17/EGLVL-k0 were mixed by a method known to those skilled in the art using the difference in charge in the constant regions (Proc. Natl. Acad. Sci., 110, 5145-5150, 2013) to prepare the bispecific antibody of interest.

Assay was done by addition of mixed antibody-half molecules A1 and B1, A2 and B2, A3 and B3, A4 and B4, and A5 and B5. In the cases of A1+B1, A4+B4, and A5+B5, ADCC activity was low against SK-pca60 and SKE-4B2, but a strong ADCC activity was shown against EREG_SK-pca60_#2. In the cases of A2+B2 and A3+B3, the ADCC activity was low against SKE-4B2, but a strong ADCC activity was shown against SK-pca60 and EREG_SK-pca60_#2. When the existing bispecific antibody was used, a strong ADCC activity was shown against all the cells of SK-pca60, SKE-4B2, and EREG_SK-pca60_#2. Based on the above, it was revealed that the antibody-half molecules A1, A4, and A5, and B1, B4, and B5 prepared this time had more selective cytotoxic activity against the double-positive cell over both cells than the existing bispecific antibody, and it was also revealed that the antibody-half molecules A2 and A3, and B2 and B3 had more selective cytotoxic activity against the double-positive cell over one type of cell than the existing bispecific antibody.

Example 5

Evaluation of the Interaction Between Antibody-Half Molecules

The interaction between these antibody-half molecules A1 and B1, A2 and B2, A3 and B3, A4 and B4, or A5 and B5 was measured according to the method described in Test Example 5 using Biacore (registered trademark). At this time, for the antibody-half molecules to be captured, PF1H (SEQ ID NO: 22), which is the H chain variable region portion of the anti-human IL6 receptor antibody described in WO 2009/041621, was used as the H chain variable region portion, PF1L (SEQ ID NO: 23), which is the L chain variable region portion of the anti-human IL6 receptor antibody described in WO 2009/041621, was used as the L chain variable region portion, and k0 was used as the L chain constant region portion. In addition, for the antibody-half molecules used as analytes, IC17H (SEQ ID NO: 24), which is the anti-KLH antibody described in WO 2015/174439, was used as the H chain variable region, IC17L (SEQ ID NO: 25), which is the anti-KLH antibody described in WO 2015/174439, was used as the L chain variable region, and k0 was used as the L chain constant region.

As a result, as shown in Table 3, when approximately 50 RU of the antibody-half molecule A1-A5 was captured, it was demonstrated that double-positive cell-selective ADCC activity was exerted when the molar binding ratio of the antibody-half molecules B1-B5 was 0.18 to 0.63.

TABLE 3

| B1/A1 | B2/A2 | B3/A3 | B4/A4 | B5/A5 |
|-------|-------|-------|-------|-------|
| 0.38  | 0.63  | 0.54  | 0.25  | 0.27  |

Example 6

In Vivo Evaluation of Antibody-Half Molecules

Using antibody-half molecules with the variable region portions of anti-mouse CD19 antibody, it was evaluated whether antibody-half molecules DA303v2 and DB220v2 form a dimer and show cytotoxic activity only when they bind to antigens in mice in vivo.

6-1. Preparation of Anti-Mouse CD19 Antibody-Half Molecules

For the anti-mouse CD19 antibody (Clone: 1D3), the cell line HB-305 was purchased from ATCC and the antibody gene was cloned by a method known to those skilled in the art. A gene was prepared for an antibody-half molecule H chain having the H chain variable region of the anti-mouse CD19 antibody and having DA303v2 (SEQ ID NO: 27) as the antibody-half molecule H chain constant region portion, which is a constant region portion prepared by introducing the modifications L234Y/L235Q/G236W/S239M/H268D/D270E/S298A for enhancing ADCC and the modifications D356K/V397Y/K409D for promoting antibody-half molecule formation and heterodimerization into the CH2 and CH3, respectively, of G1d (SEQ ID NO: 26), which is wild-type human IgG1 from which C-terminal Gly and Lys are removed. Likewise, a gene was prepared for an antibody-half molecule H chain having the H chain variable region of the anti-mouse CD19 antibody and having DB220v2 (SEQ ID NO: 28) as the antibody H chain constant region portion, which is a constant region portion prepared by introducing the modifications D270E/K326D/A330M/K334E for enhancing ADCC and the modifications V397Y/K409D/K439E for promoting antibody-half molecule-formation and heterodimerization into the CH2 and CH3, respectively, of G1d. In addition, in order to prepare a whole antibody having the same ADCC-enhancing modifications as those of these antibody-half molecules, genes were prepared for an antibody H chain having the H chain variable region of the anti-mouse CD19 antibody and having Kn125 (SEQ ID NO: 29) as the antibody H chain constant region, which was prepared by introducing the ADCC-enhancing modifications L234Y/L235Q/G236W/S239M/H268D/D270E/S298A and the heterodimerization modifications Y349C/T366W into the CH2 and CH3 of G1d, respectively, and for an antibody H chain having the H chain variable region of the anti-mouse CD19 antibody and having H1076 (SEQ ID NO: 30) as the antibody H chain constant region, which was prepared by introducing the ADCC-enhancing modifications D270E/K326D/A330M/K334E and the heterodimerization modifications D356C/T366S/L368A/Y407V into the CH2 and CH3 of G1d, respectively. The knobs-into-holes technique (Margaret Merchant et al., Nature Biotechnology 1998, 16, 677-681) has been introduced into Kn125 and H1076, and therefore co-expression of these two H chain genes with an gene for the L chain of the anti-mouse CD19 antibody results in a heterodimerized whole antibody being produced. Similarly, genes were also prepared for an antibody H chain having the H chain variable region of the anti-mouse CD19 antibody and having F760 (SEQ ID NO: 31) as the H chain constant region, which is a constant region prepared by introducing the modifications for attenuating the binding to mouse FcγR described in WO 2013/047748 (L235R/S239K) into G1d; and for an antibody H chain having the H chain variable region of the anti-mouse CD19 antibody and having mouse IgG2a constant region with enhanced ADCC activity described in WO 2015/174439 (mFa55: SEQ ID NO: 32). As an antibody not binding to mouse CD19, a gene for an antibody H chain having IC17H (SEQ ID NO: 24), which is the H chain variable region of the anti-KLH antibody described in WO 2015/174439, and having F760nN17 (SEQ ID NO: 33), which is a constant region with attenuated binding to FcγR, was prepared, respectively. As antibody L chains, genes for an antibody L chain having a wild-type human kappa constant region (k0: SEQ ID NO: 14) and the L chain variable region of the anti-mouse CD19 antibody, and for an antibody L chain having a wild-type mouse kappa constant region (mk0: SEQ ID NO: 34) and the L chain variable region of the anti-mouse CD19 antibody, were prepared. Moreover, a gene for an antibody L chain having the anti-KLH antibody L chain variable region IC17L (SEQ ID NO: 25) and a wild-type human kappa constant region (k0) was prepared. The respective genes thus prepared were expressed in the combinations shown in Table 4, and the antibodies of interest were obtained by the method described in Test Example 1.

TABLE 4

| | Composition of each domain in in vivo B cell depletion | | | | |
|---|---|---|---|---|---|
| Name of Antibody-half molecules | H chain variable region portion | H chain constant region portion 1 | H cahin constant region portion 2 | L chain variable region portion | L chain constant region portion |
| 1D3-mFa55 | anti-mouse CD19 | mFa55 | | anti-mouse CD19 | mk0 |
| 1D3-Kn125/HI076 | anti-mouse CD19 | Kn125 | HI076 | anti-mouse CD19 | k0 |
| 1D3-DA303v2 | anti-mouse CD19 | DA303v2 | | anti-mouse CD19 | k0 |
| 1D3-DB220v2 | anti-mouse CD19 | DB220v2 | | anti-mouse CD19 | k0 |
| 1D3-F760 | anti-mouse CD19 | F760 | | anti-mouse CD19 | k0 |
| KLH-F760nN17 | anti-KLH | F760nN17 | | anti-KLH | k0 |

6-2. Evaluation of the Binding of Anti-Mouse CD19 Antibody-Half Molecules or Dimers Thereof to Mouse FcγR Of the antibody-half molecules prepared in Example 6-1, 1D3-mFa55, 1D3-Kn125/H1076, 1D3-DA303v2, 1D3-DB220v2, and a mixture of equal amounts of 1D3-DA303v2 and 1D3-DB220v2 were assayed for binding to mouse FcγRI, II, III, and IV. Further, as a reference, anti-mouse CD19 antibody-half molecule 1D3-G1d was obtained according to the method of Test Example 1 by preparing a gene for an antibody-half molecule H chain having the H chain variable region portion of the anti-mouse CD19 antibody and having the H chain constant region G1d obtained by removing C-terminal Gly and Lys from the sequence of wild-type human IgG1, and a gene for an antibody L chain having the wild-type human kappa constant region k0 and the L chain variable region of the anti-mouse CD19 antibody. Mouse FcγRI, II, III, and IV were prepared by the method described in WO 2014/030750. Interaction analysis of each antibody-half molecule or dimer thereof with FcγR was performed using Biacore (registered trademark) T200 (GE Healthcare). The used running buffer was HBS-EP+ 10X (GE Healthcare) diluted to ¹/₁₀th, and assay temperature was 25° C. The chip used was Series S Sensor Chip CM5 (GE Healthcare) on which Protein A/G (PIERCE) was immobilized by the amine coupling method. Assay was performed by capturing a antibody-half molecule of interest on this sensor chip and allowing the molecule to interact with FcγR diluted with the running buffer. The antibody-half molecule captured on the sensor chip was washed off and the sensor chip was regenerated by reaction with 25 mM NaOH and with 10 mM Glycine-HCl (pH 1.5), and the sensor chip was reused. The kinetic analysis for calculating the KD value for each antibody-half molecule or its dimer for FcγR was carried out according to the following method. First, the antibody-half molecule of interest was captured onto the above sensor chip and mFcγR diluted with the running buffer was allowed to interact. For the obtained sensorgram, the measurement results were globally fitted with a 1:1 Langmuir binding model using Biacore (registered trademark) Evaluation Software to calculate the association rate constant ka (L/mol/s) and the dissociation rate constant kd (1/s). From these values, the dissociation constant KD (mol/L) was calculated. In addition, when it was judged that the interaction between the antibody-half molecule or its dimer and FcγR was so weak that it could not be correctly analyzed by the above kinetic analysis, the KD for that interaction was calculated using the following 1:1 binding model formula described in Biacore (registered trademark) T100 Software Handbook BR1006-48 Edition AE.

antibody-half molecule or dimer thereof, as compared to G1d, the maximum amount of each FcγR that can bind is unchanged, and the $R_{max}$ at the time of measurement is in proportion to the amount of the antibody bound on the chip at that time of measurement. $R_{eq}$ was the amount of binding of each FcγR observed at the time of measurement to the antibody-half molecule or dimer thereof on the sensor chip.

The thus obtained KD values of each antibody for mouse FcγRs are shown in Table 5. Values italicized in the table were calculated using the above Formula 4, because it was judged that the binding of FcγR to the antibody-half molecule or dimer thereof was so weak that it could not be correctly analyzed by kinetic analysis. The value of "KD fold for mouse FcγRs" is the value obtained by dividing the KD of G1d for each FcγR by the KD of each antibody, and indicates how much the affinity of each antibody for each FcγR was enhanced or weakened as compared to G1d. N.D. indicates that no binding was observed on the sensorgram.

TABLE 5

| Name of antibody or antibody-half molecule | Result of the affinity measurement for mouse FcγRs | | | | | | | |
|---|---|---|---|---|---|---|---|---|
| | KD (M) for mouse Fc γ Rs | | | | KD fold for mouse Fc γ Rs (G1d = 1) | | | |
| | Fc γ RI | Fc γ RII | Fc γ RIII | Fc γ RIV | Fc γ RI | Fc γ RII | Fc γ RIII | Fc γ RIV |
| 1D3-G1d | 1.23E−07 | 1.90E−06 | 4.97E−06 | 1.73E−07 | 1.00 | 1.00 | 1.00 | 1.00 |
| 1D3-mFa55 | 2.75E−09 | 5.52E−07 | 4.25E−07 | 3.01E−09 | 44.73 | 3.44 | 11.69 | 57.48 |
| 1D3-Kn125/HI076 | 2.80E−07 | 3.31E−07 | 3.77E−07 | 6.83E−10 | 0.44 | 5.74 | 13.18 | 253.29 |
| 1D3-DA303v2 | N.D. | N.D. | N.D. | N.D. | — | — | — | — |
| 1D3-DB220v2 | 2.62E−06 | 6.37E−05 | 1.38E−04 | N.D. | 0.05 | 0.03 | 0.04 | — |
| 1D3-DA303v2/1D3−DB220v2 | 3.84E−06 | 2.31E−05 | 1.24E−05 | 1.50E−08 | 0.03 | 0.08 | 0.40 | 11.53 |

The behavior of molecules interacting in the 1:1 binding model on Biacore (registered trademark) can be represented by the following Formula 3.

$$R_{eq}=C \cdot R_{max}/(KD+C)+RI \quad \text{(Formula 3)}$$

$R_{eq}$: a plot of steady state binding level against analyte concentration
C: concentration
RI: bulk refractive index contribution in the sample
$R_{max}$: analyte binding capacity of the surface When this Formula is transformed, KD can be expressed as the following Formula 4.

$$KD=C \cdot R_{Max}/(R_{eq}-RI)-C \quad \text{(Formula 4)}$$

It is possible to calculate KD by substituting the values of $R_{max}$, RI, and C into this Formula. The values of RI and C can be obtained from the sensorgram resulting from the measurement and the measurement conditions. $R_{max}$ was calculated in accordance with the following method. For the reference antibody showing sufficiently strong interaction that was evaluated simultaneously in that measurement round, an $R_{max}$ value was obtained by global fitting with the above-mentioned 1:1 Langmuir binding model. This $R_{max}$ value was divided by the amount of the reference antibody captured to the sensor chip and multiplied by the captured amount of the modified antibody to be evaluated. The resulting value was used as $R_{max}$. Under the present measurement conditions, RI=0, C=500 nM (FcγRI, FcγRIV) or 4000 nM (FcγRII, FcγRIII). For $R_{max}$, the value of $R_{max}$ obtained by performing global fitting with a 1:1 Langmuir binding model on the sensorgram resulting from analyzing the interaction of G1d with each FcγR was divided by the captured amount of G1d, and multiplied by the captured amount of each antibody to obtain an $R_{max}$ value. This calculation is based on the assumption that in whichever From the results in Table 5, mFa55, which is an FcγR binding-enhanced mouse IgG2a antibody, showed a binding enhancement of 44.7 folds to FcγRI, 3.4 folds to FcγRII, 11.7 folds to FcγRIII, and 57.5 folds to FcγRIV as compared to G1d. Kn125/H1076, a heterodimerized ADCC-enhanced antibody of human IgG1 type, showed a weakened binding by 0.4 folds to FcγRI, and a binding enhancement of 5.7 folds to FcγRII, 13.2 folds to FcγRIII, and 253.3 folds to FcγRIV, as compared to G1d. The antibody-half molecule DA303v2 did not bind to any mouse FcγR. The binding of the antibody-half molecule DB220v2 to any mouse FcγR was also weakened, and its affinity was 0.05 folds to FcγRI, 0.03 folds to FcγRII, and 0.04 folds to FcγRIII, as compared to G1d. It did not bind to FcγRIV. When measuring 1D3-DA303v2/1D3-DB220v2 prepared by mixing equal amounts of the two antibody-half molecules DA303v2 and DB220v2, although the binding was weakened by 0.03 folds to FcγRI, 0.08 folds to FcγRII, and 0.4 folds to FcγRIII, the binding was enhanced by 11.5 folds to FcγRIV, as compared to G1d. Based on the above results, although either antibody-half molecule alone has almost no FcγR-binding activity, the two antibody-half molecules are expected to show effector activity due to the enhanced binding to FcγRIV when they are mixed and form a heterodimer.

Figures 1, 2, 3:
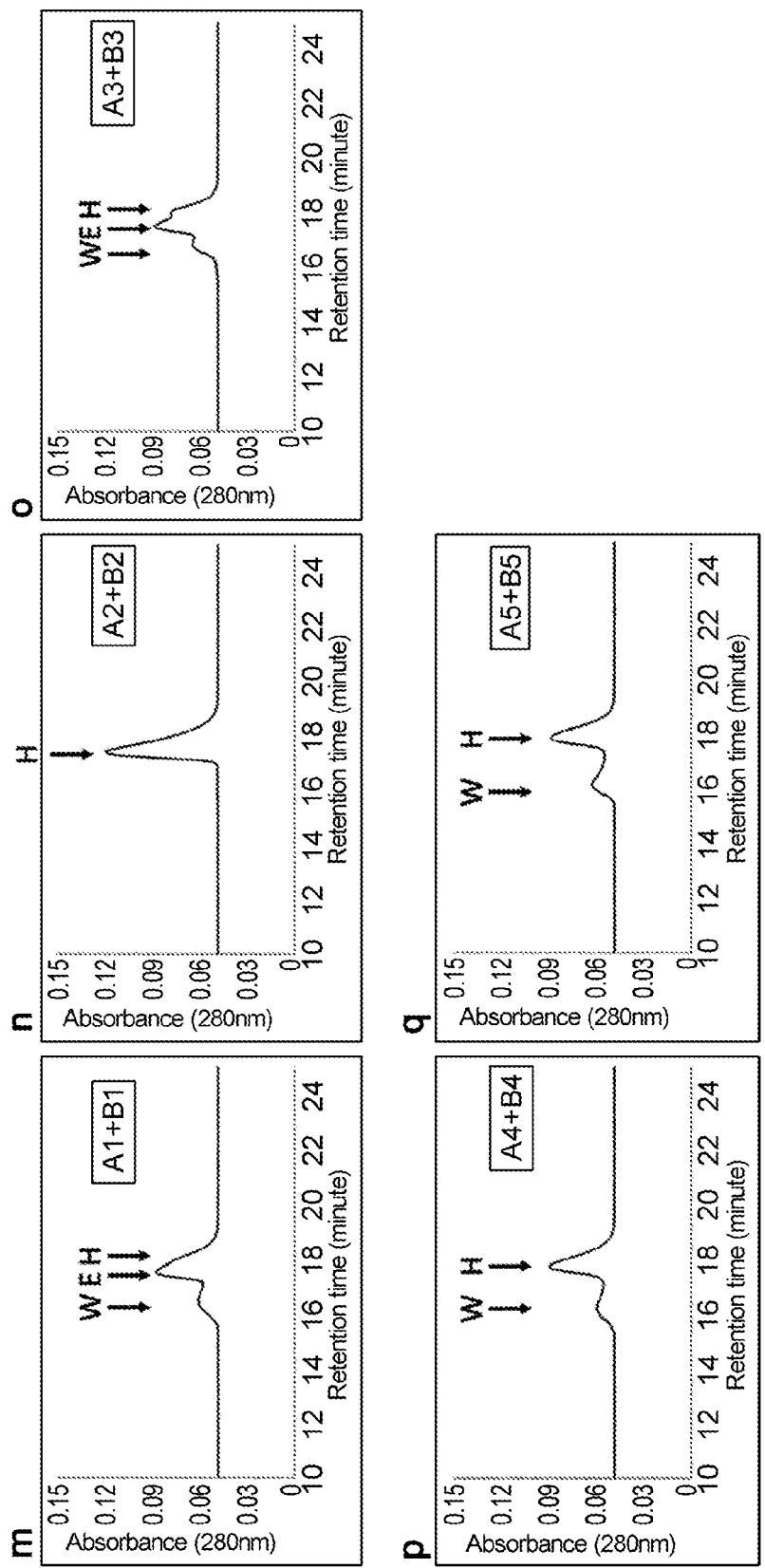
Figure 2:
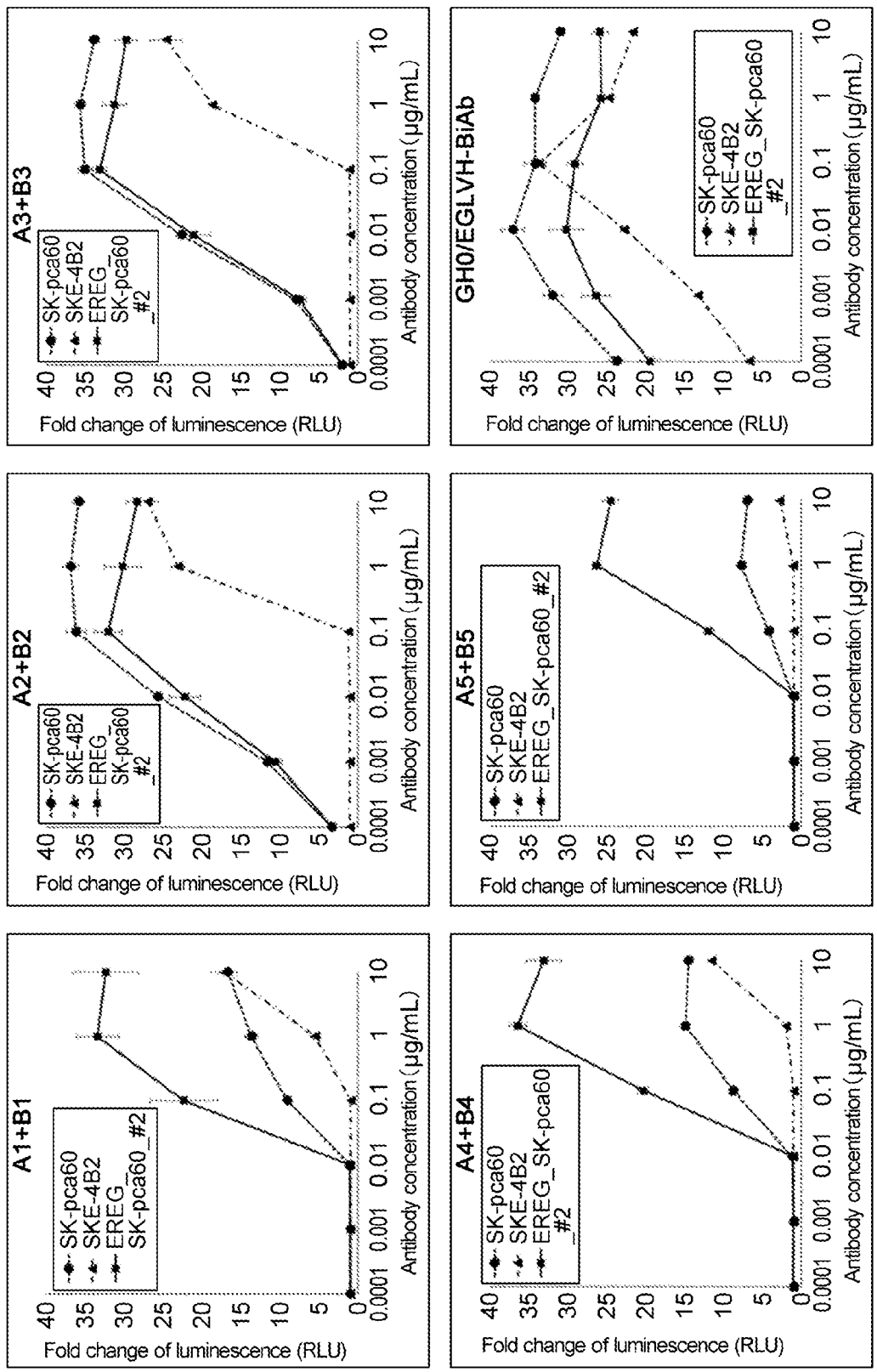
Figure 3:
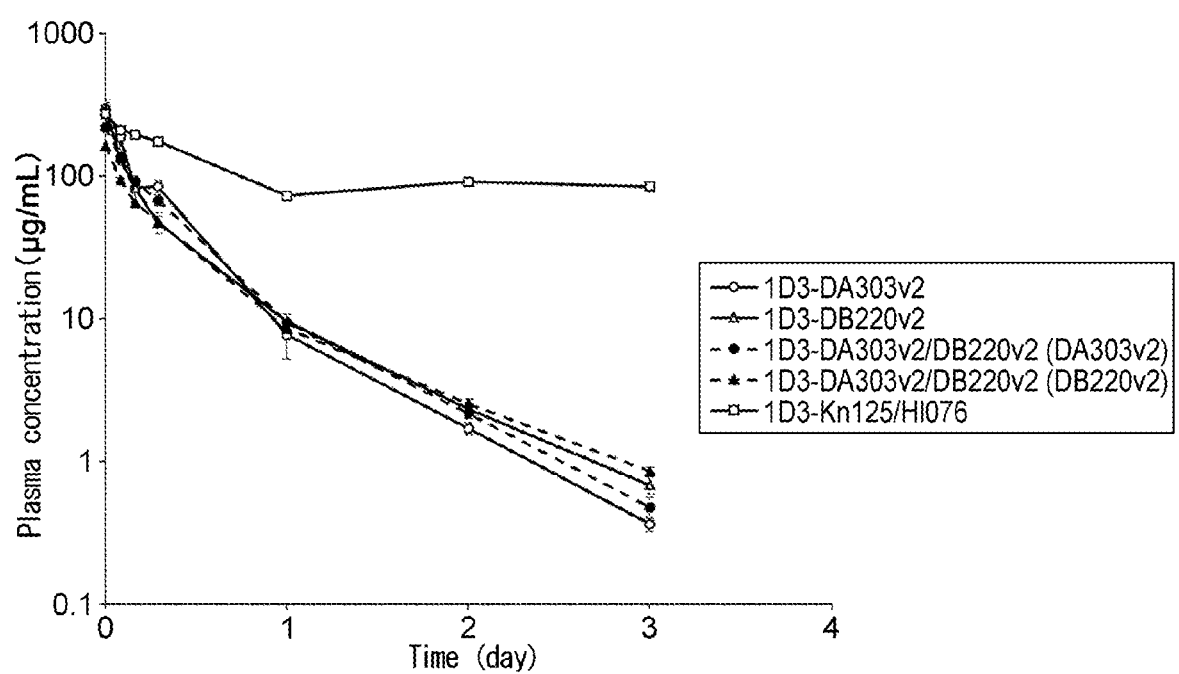

6-3. Pharmacokinetic Evaluation of Antibody-Half Molecules when Administered Alone and Administered in Combination to Mouse Pharmacokinetics in murine blood of 1D3-Kn125/H1076, 1D3-DA303v2, 1D3-DB220v2, and 1D3-DA303v2/DB220v2 prepared by the method described in Example 6-1 was evaluated. The administration was carried out from the mouse tail vein at 10 mg/kg, and blood was taken over time from the jugular vein. Plasma concentration of antibody-half molecule was determined by electrochemiluminescence immunoassay (ECLIA: Test Example 6) for 1D3-Kn125/H1076, 1D3-DA303v2 and 1D3-DB220v2, and by LC-MS (Test Example 7) for 1D3-DA303v2/DB220v2, respectively. As a result, 1D3-DA303v2, 1D3-DB220v2, and 1D3-DA303v2/DB220v2 disappeared from blood much faster than the whole antibody 1D3-Kn125/H1076, and decreased to about 1/100th of the concentration immediately after administration on day 3 after administration (FIG. 3). In addition, for 1D3-DA303v2 and 1D3-DB220v2, it was shown that there was no significant difference in the change in their plasma concentrations between when each was administered alone and when both were administered in combination. This suggests that even when administered in combination, the antibody-half molecules are present alone without heterodimerization and that they are heterodimerized only when bound to the antigen by their variable regions.

6-4. Evaluation of B Cell Depletion in Mouse In Vivo

Figure 4:
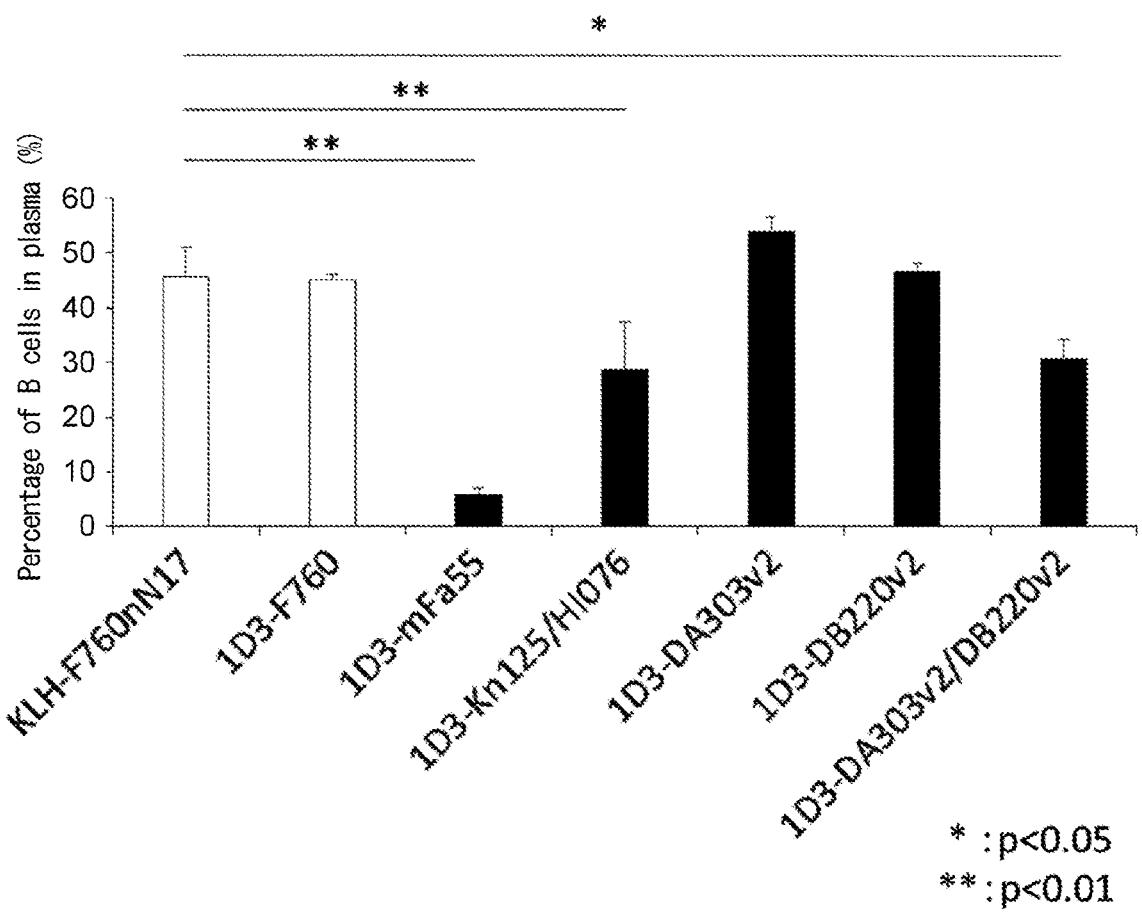
FIG. 4 is a graph showing FACS quantification of the proportion of B cells in blood of normal mice to which antibody-half molecules or a whole antibody having a variable region for mouse CD19 was administered.

The cytotoxic activity was verified by intravenously administering to mice the anti-mouse CD19 antibody-half molecules (described in Table 4) purified and prepared by the method described in Example 6-1. The dose in the in vivo B cell depletion test was set, from the disappearance concentration profiles of the whole antibody and antibody-half molecules shown in Example 6-3, such that the trough concentrations would become comparable with each other in each specimen. Specifically, each antibody or antibody-half molecule was intravenously administered to C57BL/6NCr Slc mice under the administration conditions shown in Table 6 in order to maintain necessary blood concentrations (n=3 in each group). On the third day after the administration, blood was sampled from the dorsal metatarsal vein, B cells in blood were stained by the method described in Test Example 8, and B cells in viable cells were detected with FACS. The percentage of B cells in blood was calculated by the method described in Test Example 9. As a result, as compared to KLH-F760nN17, 1D3-F760 showed no cytotoxic activity, and 1D3-mFa55 and 1D3-Kn125/H1076, which were the positive controls, showed significant cytotoxic activity. Under these conditions, although the antibody-half molecules 1D3-DA303v2 and 1D3-DB220v2 did not show cytotoxic activity when each was administered alone, they showed significant cytotoxic activity as compared to KLH-F760nN17 when they were mixed in equal amounts and administered (FIG. 4). As shown in Example 6-3, even if the antibody-half molecules are administered in combination, it is thought that they exist as antibody-half molecules unless their variable regions bind to the antigen. Therefore, the B cell depletion activity obtained here is considered to be the result of ADCC activity exerted by the respective antibody-half molecules which formed a heterodimer only after binding to the antigen by their variable regions.

TABLE 6

Anti-CD19 antibody administration group settings

| Group No | Antibody Name | Administration concentration [mg/kg] | Administration Frequency | n |
|---|---|---|---|---|
| 1 | KLH-F760nN17 | 10 | 1 shot | 3 |
| 2 | 1D3-F760 | 10 | 1 shot | 3 |
| 3 | 1D3-mFa55 | 10 | 1 shot | 3 |
| 4 | 1D3-Kn125/H1076 | 10 | 1 shot | 3 |
| 5 | 1D3-DA303v2 | 70.3 | QD × 3shot | 3 |

TABLE 6-continued

Anti-CD19 antibody administration group settings

| Group No | Antibody Name | Administration concentration [mg/kg] | Administration Frequency | n |
|---|---|---|---|---|
| 6 | 1D3-DB220v2 | 70.3 | QD × 3shot | 3 |
| 7 | 1D3-DA303v2/DB220v2 | 70.3/70.3 | QD × 3shot | 3 |

Test Example 10

Preparation of Antibody-Half Molecule Expression Vectors and Expression and Purification of Antibody-Half Molecules Introduction of amino acid substitutions was carried out by a method known to those skilled in the art using QuikChange Site-Directed Mutagenesis Kit (Stratagene), PCR or In-fusion Advantage PCR cloning kit (TAKARA) and the like to construct expression vectors. The nucleotide sequences of the obtained expression vectors were determined by a method known to those skilled in the art. The prepared plasmids were transiently introduced into Expi293 cells (Invitrogen) to express antibody-half molecules. Antibody-half molecules were purified from the obtained culture supernatants by a method known to those skilled in the art using MonoSpin ProA 96-well plate type (registered trademark) (GL Science). The concentrations of the purified antibody-half molecules were calculated by measuring the absorbance at 280 nm using a spectrophotometer and calculating the antibody-half molecule concentrations from the obtained values using the extinction coefficient calculated by the PACE method (Protein Science 1995; 4: 2411-2423).

Test Example 11

Analysis of the Molecular Weight of Antibody-Half Molecules

The molecular weight of the obtained antibody-half molecules was analyzed by a method known to those skilled in the art using ACQUITY UPLC H-Class (registered trademark) (Waters), an HPLC, and using SuperSW3000 (TOSOH) as column. The antibody-half molecule concentration was 0.10 mg/mL, and 10 μL was injected.

Example 7

Preparation of Antibody-Half Molecules

To verify whether homodimer formation can be suppressed without using the heterodimerization modifications used in Example 1, heterodimerization modifications were not used, or the modifications reported by Ha et al. were used (Ha J H, Kim J E, Kim Y S (2016) Immunoglobulin Fc Heterodimer Platform Technology: From Design to Applications in Therapeutic Antibodies and Proteins. Front Immunol. 2016 Oct. 6; 7:394). Specifically, half molecule antibodies A and B with ADCC-enhancing modifications, hinge region modifications, and CH3 interface destabilization modifications only were used. In addition, the substitutions Y349T and T394F and the substitutions S364H and F405A were introduced into antibody-half molecule A and antibody-half molecule B, respectively. Abbreviations and names of the antibody-half molecules prepared and evaluated, CH3 modifications, and SEQ ID NOs of antibody-half molecules are shown in Table 7.

TABLE 7

| Abbre-viation | Name | CH3 modifications | SEQ ID NO |
|---|---|---|---|
| A6 | MRAH-DA303v2.n.n | V397Y/K409D | 35 |
| A7 | MRAH-DA303v2.n.n.HATF.B | V397Y/K409D/Y349T/T394F | 36 |
| B6 | MRAH-DB220v2.n.n | V397Y/K409D | 37 |
| B7 | MRAH-DB220v2.n.n.HATF.A | V397Y/K409D/S364H/F405A | 38 |

Example 8

Evaluation of the Molecular Weight of Antibody-Half Molecules

The molecular weight of the prepared antibody-half molecules A and B was evaluated by size exclusion chromatography. At this time, the antibody against the human interleukin 6 receptor disclosed in WO 2009/125825 was used as the whole antibody control (peak W in FIG. 5-1a). MRAH (SEQ ID NO: 11) was used as the H chain variable region and the sequence of the wild-type IgG1 (SEQ ID NO: 12) was used as the H chain constant region. MRAL (SEQ ID NO: 13) was used as the L chain variable region, and the sequence of k0 (SEQ ID NO: 14), which is a wild-type κ chain, was used as the L chain constant region. As the antibody-half molecule state control (peak H in FIG. 5b), EGLVH (SEQ ID NO: 15), which is the H chain variable region portion of the anti-human epiregulin antibody described in WO 2013/100120, was used as the H chain variable region, and wtIgG4C4 (SEQ ID NO: 16) having the modification described by Lu et al. (Shan L, Colazet M, Rosenthal K L, Yu X Q, Bee J S, Ferguson A, Damschroder M M, Wu H, Dall'Acqua W F, Tsui P, Oganesyan V in Generation and Characterization of an IgG 4 Monomeric Fc Platform. PLOS One. 2016 Aug. 1; 11 (8)) was used as the H chain constant region portion. EGLVL (SEQ ID NO: 17), which is the L chain variable region portion of the anti-human epiregulin antibody described in WO 2013/100120, was used as the L chain variable region, and the sequence of k0, which is a wild-type κ chain, was used as the L chain constant region. The assay was carried out according to the method described in Test Example 11. In this case, MRAH was used for each of the H chain variable regions, and MRAL-k0 was used for all of the L chains.

Figures 1, 5:
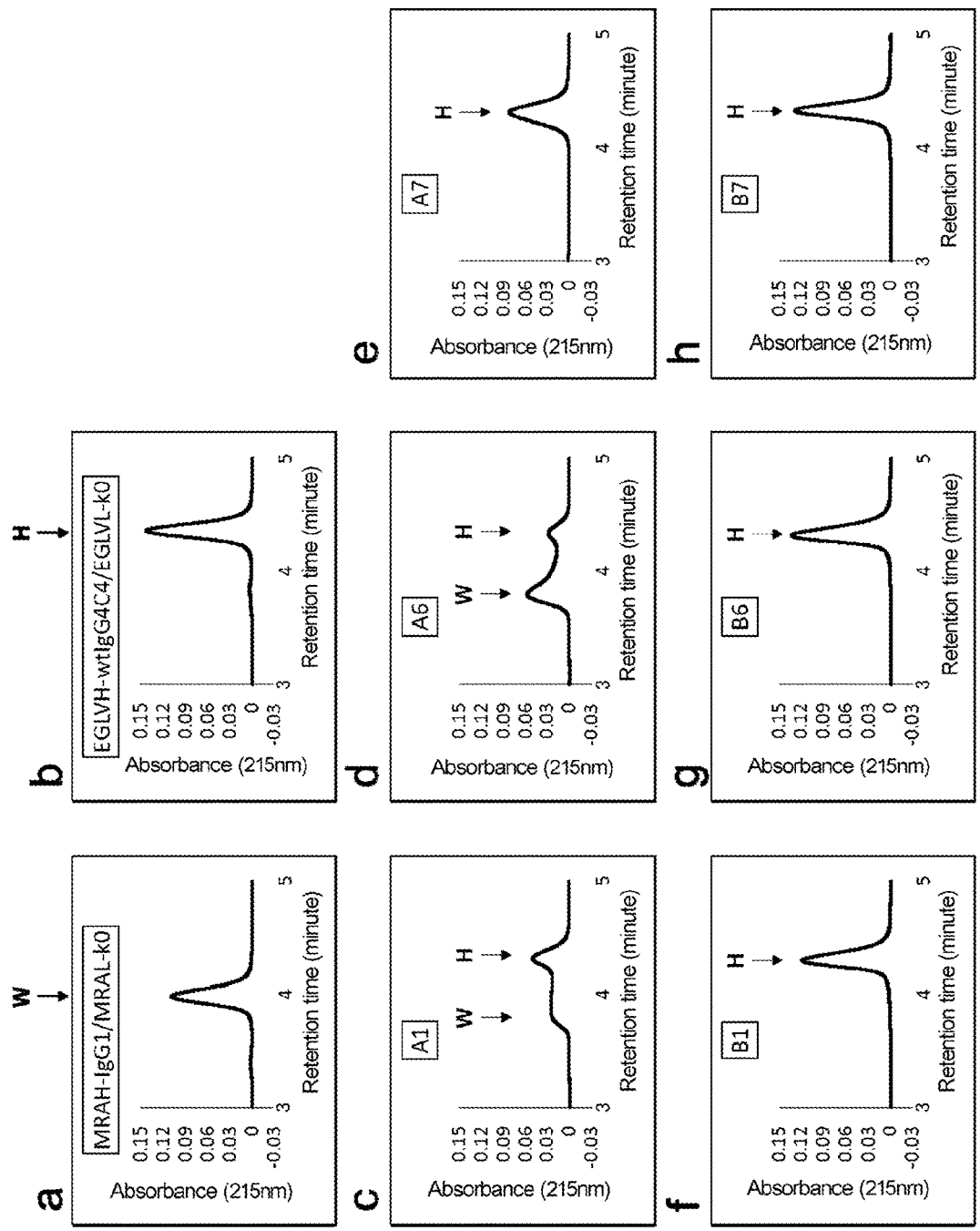
Figures 2, 5:
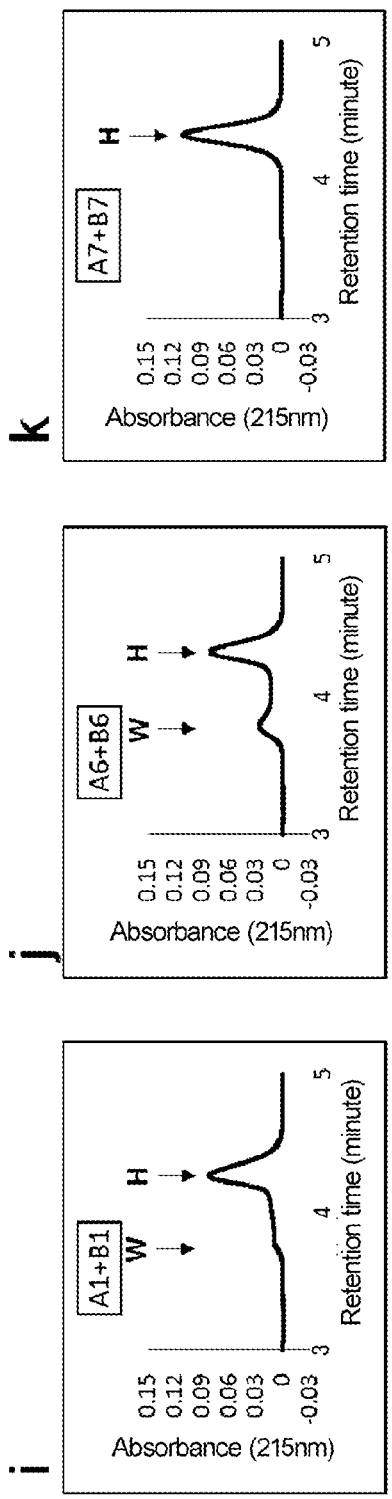

As a result of the assay, as shown in FIG. 5, in the case of antibody-half molecule A1 or A6 alone, a mixture of the antibody-half molecule (peak H peak) and the whole antibody (peak W) was obtained (FIGS. 5c and 5d). Antibody-half molecule A7, B1, B6, or B7 alone existed as an antibody-half molecule (peak H) (FIGS. 5e to 5h). In addition, even when antibody-half molecules A1 and B1 (FIG. 5i), A6 and B6 (FIG. 5j), and A7 and B7 (FIG. 5k) were mixed, formation of the whole antibody (peak W) was not increased as compared to the case of antibody-half molecule A1, A6 or A7 alone or antibody-half molecule B1, B6, or B7 alone, respectively.

Example 9

Evaluation of ADCC Activity of Antibody-Half Molecules

It was assayed according to the method described in Test Example 4 whether antibody-half molecules with these constant regions have superior double-positive cell-selective cytotoxic activity relative to an existing bispecific antibody.

As antigen-expressing cells, SK-pca60 and SKE-4B2 described in WO 2016/182064 and WO 2014/208482, respectively, which were obtained by forcing SK-Hep1 to express glypican 3 and epiregulin, respectively, were used. As a glypican 3/epiregulin double-positive cell, EREG_SK-pca60_#2 obtained by forcing SK-pca60 to express epiregulin was used. At this time, for the series of antibody-half molecules A, the H chain variable region portion was GH0 (SEQ ID NO: 18), which is of the anti-GPC3 antibody described in WO 2009/041062, the L chain variable region portion was GL0 (SEQ ID NO: 19), which is of the anti-GPC3 antibody described in WO 2009/041062, and the L chain constant region portion was k0. For the antibody-half molecule B, EGLVH was used, EGLVL was used as the L chain variable region, and k0 was used as the L chain constant region. In addition, GH0-Kn125P17/GL0-k0//EG-LVH-H1076N17/EGLVL-k0 (GH0/EGLVH-BiAb) was used as the existing bispecific antibody. For the constant regions of the bispecific antibody, the substitutions L234Y, L235Q, G236W, S239M, H268D, D270E, and S298A and the substitutions D270E, K326D, A330M, and K334E, as described in WO2013/002362, were introduced into the CH2 of Kn125P17 (SEQ ID NO: 20) and H1076N17 (SEQ ID NO: 21), respectively, so that the ADCC activity would be enhanced upon heterodimerization. In addition, in order to prepare the bispecific antibody utilizing the difference in charge, the substitutions D356K and V397Y described in WO 2015/046467 were introduced into Kn125P17, and the substitutions V397Y and K439E were introduced into H1076N17, respectively. For the sequence at positions 356 to 358, the sequence of EEM, which is a wild-type IgG1 allotype, was used. The thus prepared GH0-Kn125P17/GL0-k0 and EGLVH-H1076N17/EGLVL-k0 were mixed by a method known to those skilled in the art using the difference in charge in the constant region (Proc. Natl. Acad. Sci., 110, 5145-5150, 2013) to prepare the bispecific antibody of interest.

Figure 6:
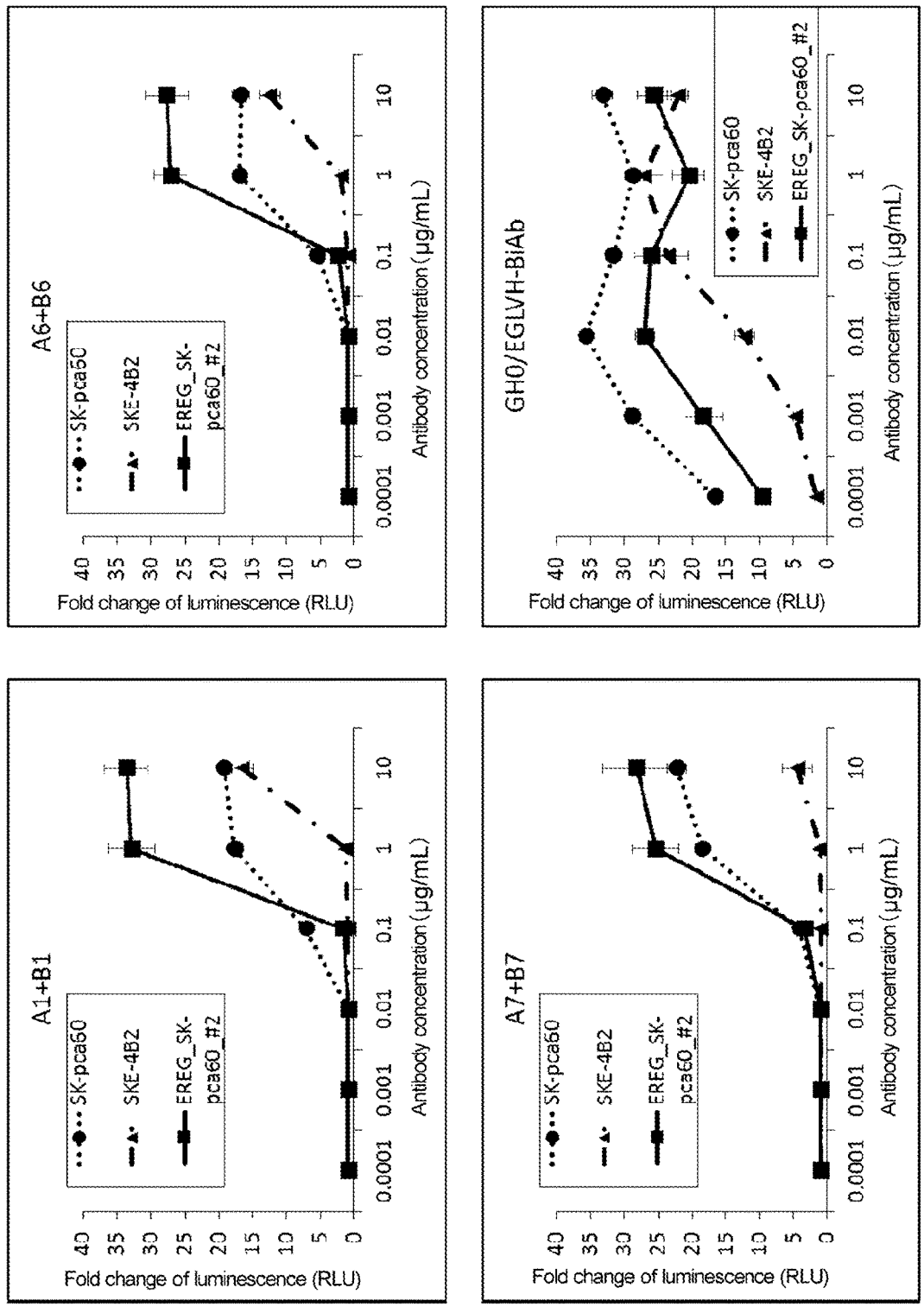
FIG. 6 shows the result of ADCC reporter assay by which ADCC activity by a combination of antibody-half molecules was examined in the presence of cells expressing two different antigens (EREG_SK-pca60_#2) or in the presence of cells expressing one antigen (SK-pca60 or SKE-4B2).

Assay was done by mixing and adding antibody-half molecules A1 and B1, A6 and B6, and A7 and B7. The assay results are shown in FIG. 6. As in the case of A1+B1, A6+B6 and A7+B7 showed low ADCC activity against SK-pca60 and SKE-4B2, but strong ADCC activity against EREG_SK-pca60_#2. When the existing bispecific antibody was used, strong ADCC activity was exhibited against all SK-pca60, SKE-4B2, and EREG_SK-pca60_#2 cells. Based on the above, it was revealed that the antibody-half molecules A6 and A7, and B6 and B7 prepared this time had more selective cytotoxic activity against the double-positive cell over both cells than the existing bispecific antibody.

Example 10

Evaluation of the Interaction Between Antibody-Half Molecules

The interaction between these antibody-half molecules A1 and B1, A6 and B6, or A7 and B7 was measured according to the method described in Test Example 5 using Biacore (registered trademark). At this time, for the antibody-half molecule to be captured, PF1H (SEQ ID NO: 22), which is the H chain variable region portion of the anti-human IL6 receptor antibody described in WO 2009/041621, was used as the H chain variable region portion, PF1L (SEQ ID NO: 23), which is the L chain variable region portion of the anti-human IL6 receptor antibody described in WO 2009/041621, was used as the L chain variable region portion, and k0 was used as the L chain constant region portion. In addition, for the antibody-half molecules used as analytes, IC17H (SEQ ID NO: 24), which is the anti-KLH antibody described in WO 2015/174439, was used as the H chain variable region, IC17L (SEQ ID NO: 25), which is the anti-KLH antibody described in WO 2015/174439, was used as the L chain variable region, and k0 was used as L chain constant region.

As a result, as shown in Table 8, it was demonstrated that when approximately 50 RU of antibody-half molecule A6 or A7 was captured, the molar binding ratio of antibody-half molecule B6 or B7 became within the range of 0.18 to 0.63, respectively, and double-positive cell-selective ADCC activity was also exerted. The dilution of antibody-half molecule B with the running buffer was 5.7 to 9.0 times in this Example, while it was 18.6 to 28.0 times in Example 5.

TABLE 8

| B1/A1 | B6/A6 | B7/A7 |
|-------|-------|-------|
| 0.54  | 0.42  | 0.32  |

The invention claimed is:

1. A first antigen-binding molecule comprising a first antigen-binding region that binds to a first antigen and a first IgG Fc domain comprising a first CH3, wherein, when mixed in solution with a second antigen-binding molecule having a second antigen-binding region that binds to a second antigen and a second IgG Fc domain comprising a second CH3, the first antigen-binding molecule is promoted to form a heterodimer with the second antigen-binding molecule and suppressed to form a homodimer of the first antigen-binding molecule, wherein the first CH3 domain comprises the D356K/V397Y/K409D, D356K/V397Y/K409H, D356K/V397Y/K409T, D356K/E357N/V397Y/K409D, D356K/E357L/V397Y/K409D, V397Y/K409D or V397Y/K409D/Y349T/T394F substitutions and the second CH3 domain comprises the V397Y/K409D/K439E, V397Y/K409H/K439E, V397Y/K409T/K439E, E357N/V397Y/K409D/K439E, E357L/V397Y/K409D/K439E, V397Y/K409D or V397Y/K409D/S364H/F405A substitutions, wherein the position of the substitutions is according to the EU numbering system, and
wherein the first and second polypeptide can form heterodimers in a surface plasmon reference assay.

2. A second antigen-binding molecule comprising a second antigen-binding region that binds to a second antigen and a second IgG Fc domain comprising a second CH3, wherein, when mixed in solution with a first antigen-binding molecule having a first antigen-binding region that binds to a first antigen and a first IgG Fc domain comprising a first CH3, the second antigen-binding molecule is promoted to form a heterodimer with the first antigen-binding molecule and suppressed to form a homodimer of the second antigen-binding molecule, wherein the first CH3 domain comprises the D356K/V397Y/K409D, D356K/V397Y/K409H, D356K/V397Y/K409T, D356K/E357N/V397Y/K409D, D356K/E357L/V397Y/K409D, V397Y/K409D or V397Y/K409D/Y349T/T394F substitutions and the second CH3 domain comprises the V397Y/K409D/K439E, V397Y/K409H/K439E, V397Y/K409T/K439E, E357N/V397Y/K409D/K439E, E357L/V397Y/K409D/K439E, V397Y/K409D or V397Y/K409D/S364H/F405A substitutions, wherein the position of the substitutions is according to the EU numbering system, and wherein the first and second polypeptide can form heterodimers in a surface plasmon reference assay.

3. A composition, comprising
   a) a first polypeptide comprising (i) a first antigen binding domain that binds to a first antigen and (ii) a first IgG Fc domain comprising a first CH3 domain, and
   b) a second polypeptide comprising (i) a second antigen binding domain that binds to a second antigen and (ii) a second IgG Fc domain comprising a first CH3 domain,
   wherein the first polypeptide and second polypeptide are not linked by a covalent bond,
   wherein the first CH3 domain comprises the D356K/V397Y/K409D, D356K/V397Y/K409H, D356K/V397Y/K409T, D356K/E357N/V397Y/K409D, D356K/E357L/V397Y/K409D, V397Y/K409D or V397Y/K409D/Y349T/T394F substitutions and the second CH3 domain comprises the V397Y/K409D/K439E, V397Y/K409H/K439E, V397Y/K409T/K439E, E357N/V397Y/K409D/K439E, E357L/V397Y/K409D/K439E, V397Y/K409D or V397Y/K409D/S364H/F405A substitutions, wherein the position of the substitutions is according to the EU numbering system, and
   wherein the first and second polypeptide can form heterodimers in a surface plasmon reference assay.

4. The composition of claim 3, wherein
   1) The first CH3 domain comprises the D356K/V397Y/K409D substitutions and the second CH3 domain comprises the V397Y/K409D/K439E substitutions,
   2) The first CH3 domain comprises the D356K/V397Y/K409H substitutions and the second CH3 domain comprises the V397Y/K409H/K439E substitutions,
   3) The first CH3 domain comprises the D356K/V397Y/K409T substitutions and the second CH3 domain comprises the V397Y/K409T/K439E substitutions,
   4) The first CH3 domain comprises the D356K/E357N/V397Y/K409D substitutions and the second CH3 domain comprises the E357N/V397Y/K409D/K439E substitutions,
   5) The first CH3 domain comprises the D356K/E357L/V397Y/K409D substitutions and the second CH3 domain comprises the E357L/V397Y/K409D/K439E substitutions,
   6) The first CH3 domain comprises the V397Y/K409D substitutions and the second CH3 domain comprises the V397Y/K409D substitutions, and
   7) The first CH3 domain comprises the V397Y/K409D/Y349T/T394F substitutions and the second CH3 domain comprises the V397Y/K409D/S364H/F405A substitutions.

5. The composition of claim 3, wherein the first antigen and the second antigen are different.

6. The composition of claim 3, wherein the first antigen binding domain comprises a first variable heavy chain region and a first variable light chain region and the second antigen binding domain comprises a second variable heavy chain region and a second variable light chain region.

7. The composition of claim 3, wherein the first and second IgG Fc domain comprises a first and second CH2 domain, respectively, wherein the first CH2 domain comprises the L234Y/L235Q/G236W/S239M/H268D/D270E/S298A substitutions, and the second CH2 domain comprises the D270E/K326D/A330M/K334E substitutions, wherein the position of the substitutions is according to the EU numbering system.

8. The composition of claim 3, wherein the first and second IgG Fc domains comprise the C226S and C229S substitutions, wherein the position of the substitutions is according to the EU numbering system.

9. The composition of claim 3, wherein the surface plasmon reference assay uses a sensor chip comprising immobilized first and second antigen.

10. The first antigen-binding molecule of claim 1, wherein
    1) The first CH3 domain comprises the D356K/V397Y/K409D substitutions and the second CH3 domain comprises the V397Y/K409D/K439E substitutions,
    2) The first CH3 domain comprises the D356K/V397Y/K409H substitutions and the second CH3 domain comprises the V397Y/K409H/K439E substitutions,
    3) The first CH3 domain comprises the D356K/V397Y/K409T substitutions and the second CH3 domain comprises the V397Y/K409T/K439E substitutions,
    4) The first CH3 domain comprises the D356K/E357N/V397Y/K409D substitutions and the second CH3 domain comprises the E357N/V397Y/K409D/K439E substitutions,
    5) The first CH3 domain comprises the D356K/E357L/V397Y/K409D substitutions and the second CH3 domain comprises the E357L/V397Y/K409D/K439E substitutions,
    6) The first CH3 domain comprises the V397Y/K409D substitutions and the second CH3 domain comprises the V397Y/K409D substitutions, and
    7) The first CH3 domain comprises the V397Y/K409D/Y349T/T394F substitutions and the second CH3 domain comprises the V397Y/K409D/S364H/F405A substitutions.

11. The first antigen-binding molecule of claim 1, wherein the first antigen and the second antigen are different.

12. The first antigen-binding molecule of claim 1, wherein the first antigen binding domain comprises a first variable heavy chain region and a first variable light chain region and the second antigen binding domain comprises a second variable heavy chain region and a second variable light chain region.

13. The first antigen-binding molecule of claim 1, wherein the first and second IgG Fc domain comprises a first and second CH2 domain, respectively, wherein the first CH2 domain comprises the L234Y/L235Q/G236W/S239M/H268D/D270E/S298A substitutions, and the second CH2 domain comprises the D270E/K326D/A330M/K334E substitutions, wherein the position of the substitutions is according to the EU numbering system.

14. The first antigen-binding molecule of claim 1, wherein the first and second IgG Fc domains comprise the C226S and C229S substitutions, wherein the position of the substitutions is according to the EU numbering system.

15. The first antigen-binding molecule of claim 1, wherein the surface plasmon reference assay uses a sensor chip comprising immobilized first and second antigen.

16. The second antigen-binding molecule of claim 2, wherein
1) The first CH3 domain comprises the D356K/V397Y/K409D substitutions and the second CH3 domain comprises the V397Y/K409D/K439E substitutions,
2) The first CH3 domain comprises the D356K/V397Y/K409H substitutions and the second CH3 domain comprises the V397Y/K409H/K439E substitutions,
3) The first CH3 domain comprises the D356K/V397Y/K409T substitutions and the second CH3 domain comprises the V397Y/K409T/K439E substitutions,
4) The first CH3 domain comprises the D356K/E357N/V397Y/K409D substitutions and the second CH3 domain comprises the E357N/V397Y/K409D/K439E substitutions,
5) The first CH3 domain comprises the D356K/E357L/V397Y/K409D substitutions and the second CH3 domain comprises the E357L/V397Y/K409D/K439E substitutions,
6) The first CH3 domain comprises the V397Y/K409D substitutions and the second CH3 domain comprises the V397Y/K409D substitutions, and
7) The first CH3 domain comprises the V397Y/K409D/Y349T/T394F substitutions and the second CH3 domain comprises the V397Y/K409D/S364H/F405A substitutions.

17. The second antigen-binding molecule of claim 2, wherein the first antigen and the second antigen are different.

18. The second antigen-binding molecule of claim 2, wherein the first antigen binding domain comprises a first variable heavy chain region and a first variable light chain region and the second antigen binding domain comprises a second variable heavy chain region and a second variable light chain region.

19. The second antigen-binding molecule of claim 2, wherein the first and second IgG Fc domain comprises a first and second CH2 domain, respectively, wherein the first CH2 domain comprises the L234Y/L235Q/G236W/S239M/H268D/D270E/S298A substitutions, and the second CH2 domain comprises the D270E/K326D/A330M/K334E substitutions, wherein the position of the substitutions is according to the EU numbering system.

20. The second antigen-binding molecule of claim 2, wherein the first and second IgG Fc domains comprise the C226S and C229S substitutions, wherein the position of the substitutions is according to the EU numbering system.

21. The second antigen-binding molecule of claim 2, wherein the surface plasmon reference assay uses a sensor chip comprising immobilized first and second antigen.

* * * * *

SEQUENCE LISTING

<160> NUMBER OF SEQ ID NOS: 38

<210> SEQ ID NO 1
<211> LENGTH: 447
<212> TYPE: PRT
<213> ORGANISM: Artificial sequence
<220> FEATURE:
<223> OTHER INFORMATION: MRAH-DA303v2

<400> SEQUENCE: 1

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
            435                 440                 445

<210> SEQ ID NO 2
<211> LENGTH: 447
<212> TYPE: PRT
<213> ORGANISM: Artificial sequence
<220> FEATURE:
<223> OTHER INFORMATION: MRAH-DA402v2

<400> SEQUENCE: 2

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Val Glu Pro Lys Ser Cys Asp Lys
            210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser His Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 3
<211> LENGTH: 447
<212> TYPE: PRT
<213> ORGANISM: Artificial sequence
<220> FEATURE:
<223> OTHER INFORMATION: MRAH-DA405v2

<400> SEQUENCE: 3

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Thr Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 4
<211> LENGTH: 447
<212> TYPE: PRT
<213> ORGANISM: Artificial sequence
<220> FEATURE:
<223> OTHER INFORMATION: MRAH-DA424v2

<400> SEQUENCE: 4

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Asn Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 5
<211> LENGTH: 447

<212> TYPE: PRT
<213> ORGANISM: Artificial sequence
<220> FEATURE:
<223> OTHER INFORMATION: MRAH-DA430v2

<400> SEQUENCE: 5

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Leu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

```
Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
        435                 440                 445

<210> SEQ ID NO 6
<211> LENGTH: 447
<212> TYPE: PRT
<213> ORGANISM: Artificial sequence
<220> FEATURE:
<223> OTHER INFORMATION: MRAH-DB220v2

<400> SEQUENCE: 6

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

-continued

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 7
<211> LENGTH: 447
<212> TYPE: PRT
<213> ORGANISM: Artificial sequence
<220> FEATURE:
<223> OTHER INFORMATION: MRAH-DB402v2

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

```
Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser His Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 8
<211> LENGTH: 447
<212> TYPE: PRT
<213> ORGANISM: Artificial sequence
<220> FEATURE:
<223> OTHER INFORMATION: MRAH-DB405v2

<400> SEQUENCE: 8

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Thr Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 9
<211> LENGTH: 447
<212> TYPE: PRT
<213> ORGANISM: Artificial sequence
<220> FEATURE:
<223> OTHER INFORMATION: MRAH-DB424v2

<400> SEQUENCE: 9

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60
```

```
Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
                 85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Asp Asn Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 10
<211> LENGTH: 447
<212> TYPE: PRT
<213> ORGANISM: Artificial sequence
<220> FEATURE:
<223> OTHER INFORMATION: MRAH-DB430v2
```

<400> SEQUENCE: 10

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Asp Leu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
```

```
                    405                 410                 415
Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445

<210> SEQ ID NO 11
<211> LENGTH: 119
<212> TYPE: PRT
<213> ORGANISM: Artificial sequence
<220> FEATURE:
<223> OTHER INFORMATION: MRAH

<400> SEQUENCE: 11

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 12
<211> LENGTH: 330
<212> TYPE: PRT
<213> ORGANISM: Homo sapiens

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 107
<212> TYPE: PRT
<213> ORGANISM: Artificial sequence
<220> FEATURE:
<223> OTHER INFORMATION: MRAL

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 14
<211> LENGTH: 107
<212> TYPE: PRT
<213> ORGANISM: Homo sapiens

<400> SEQUENCE: 14

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 15
<211> LENGTH: 116
<212> TYPE: PRT
<213> ORGANISM: Artificial sequence
<220> FEATURE:
<223> OTHER INFORMATION: EGLVH

<400> SEQUENCE: 15

Gln Asp Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
             20                  25                  30

Tyr Ile Gln Trp Val Arg Gln Ala Pro Gly Gln Gly Leu Glu Trp Met
         35                  40                  45

Gly Arg Ile Asp Pro Leu Arg Lys Gln Thr Lys Tyr Arg Glu Lys Phe
 50                  55                  60

Glu Gly Arg Val Thr Ile Thr Ala Asp Thr Ser Thr Asn Thr Ala Tyr
 65                  70                  75                  80

Met Glu Leu Ser Ser Leu Arg Ser Glu Asp Thr Ala Val Tyr Tyr Cys
                 85                  90                  95

Val Arg Ser Gly Arg Glu Phe Asp Tyr Trp Gly Gln Gly Thr Leu Val
            100                 105                 110

Thr Val Ser Ser
        115

<210> SEQ ID NO 16
<211> LENGTH: 327
<212> TYPE: PRT
<213> ORGANISM: Artificial sequence
<220> FEATURE:
<223> OTHER INFORMATION: wtIgG4C4

<400> SEQUENCE: 16

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

-continued

Glu Phe Leu Gly Gly Pro Ser Val Phe Leu Phe Pro Pro Lys Pro Lys
            115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Phe Pro Pro Ser Gln Glu Glu Met Thr Lys
225                 230                 235                 240

Asn Gln Val Ser Leu Arg Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Lys Pro Val Leu Asp Ser Asp Gly Ser Phe Arg Leu Glu Ser
    275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 17
<211> LENGTH: 106
<212> TYPE: PRT
<213> ORGANISM: Artificial sequence
<220> FEATURE:
<223> OTHER INFORMATION: EGLVL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Lys Tyr
            20                  25                  30

Ile Ala Trp Tyr Gln Gln Lys Pro Gly Gln Ala Pro Arg Leu Leu Ile
        35                  40                  45

Gln Tyr Thr Ser Thr Leu Gln Pro Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Glu Gln Leu Arg Thr
                85                  90                  95

Phe Gly Gly Gly Thr Lys Val Glu Ile Lys
            100                 105

<210> SEQ ID NO 18
<211> LENGTH: 115
<212> TYPE: PRT
<213> ORGANISM: Artificial sequence

```
<220> FEATURE:
<223> OTHER INFORMATION: GH0

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Ser Thr Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
                100                 105                 110

Val Ser Ser
        115

<210> SEQ ID NO 19
<211> LENGTH: 112
<212> TYPE: PRT
<213> ORGANISM: Artificial sequence
<220> FEATURE:
<223> OTHER INFORMATION: GL0

<400> SEQUENCE: 19

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
                100                 105                 110

<210> SEQ ID NO 20
<211> LENGTH: 328
<212> TYPE: PRT
<213> ORGANISM: Artificial sequence
<220> FEATURE:
<223> OTHER INFORMATION: Kn125P17

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Tyr Gln Trp Gly Pro Met Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Asp Glu Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Lys Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 21
<211> LENGTH: 328
<212> TYPE: PRT
<213> ORGANISM: Artificial sequence
<220> FEATURE:
<223> OTHER INFORMATION: H1076N17

<400> SEQUENCE: 21

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Asp Ala Leu Pro Met Pro Ile Glu Glu Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 22
<211> LENGTH: 119
<212> TYPE: PRT
<213> ORGANISM: Artificial sequence
<220> FEATURE:
<223> OTHER INFORMATION: PF1H

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Val Leu Ala Arg Ile Thr Ala Met Asp Tyr Trp Gly Glu Gly
            100                 105                 110
```

Thr Leu Val Thr Val Ser Ser
        115

<210> SEQ ID NO 23
<211> LENGTH: 107
<212> TYPE: PRT
<213> ORGANISM: Artificial sequence
<220> FEATURE:
<223> OTHER INFORMATION: PF1L

<400> SEQUENCE: 23

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
            100                 105

<210> SEQ ID NO 24
<211> LENGTH: 116
<212> TYPE: PRT
<213> ORGANISM: Artificial sequence
<220> FEATURE:
<223> OTHER INFORMATION: IC17H

<400> SEQUENCE: 24

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
            100                 105                 110

Thr Val Ser Ser
        115

<210> SEQ ID NO 25
<211> LENGTH: 107
<212> TYPE: PRT
<213> ORGANISM: Artificial sequence
<220> FEATURE:
<223> OTHER INFORMATION: IC17L

<400> SEQUENCE: 25

Asp Ile Gln Met Thr Gln Ser Ser Ser Ser Phe Ser Val Ser Leu Gly

```
 1               5                  10                 15
Asp Arg Val Thr Ile Thr Cys Lys Ala Ser Glu Asp Ile Tyr Asn Arg
                 20                 25                 30

Leu Ala Trp Tyr Gln Gln Lys Pro Gly Asn Ala Pro Arg Leu Leu Ile
             35                 40                 45

Ser Gly Ala Thr Ser Leu Glu Thr Gly Val Pro Ser Arg Phe Ser Gly
         50                 55                 60

Ser Gly Ser Gly Lys Asp Tyr Thr Leu Ser Ile Thr Ser Leu Gln Thr
65                  70                 75                 80

Glu Asp Val Ala Thr Tyr Tyr Cys Gln Gln Tyr Trp Ser Thr Pro Tyr
                 85                 90                 95

Thr Phe Gly Gly Gly Thr Lys Leu Glu Val Lys
                100                105

<210> SEQ ID NO 26
<211> LENGTH: 328
<212> TYPE: PRT
<213> ORGANISM: Artificial sequence
<220> FEATURE:
<223> OTHER INFORMATION: G1d

<400> SEQUENCE: 26

Ala Ser Thr Lys Gly Pro Ser Val Phe Pro Leu Ala Pro Ser Ser Lys
1               5                  10                 15

Ser Thr Ser Gly Gly Thr Ala Ala Leu Gly Cys Leu Val Lys Asp Tyr
                20                 25                 30

Phe Pro Glu Pro Val Thr Val Ser Trp Asn Ser Gly Ala Leu Thr Ser
             35                 40                 45

Gly Val His Thr Phe Pro Ala Val Leu Gln Ser Ser Gly Leu Tyr Ser
         50                 55                 60

Leu Ser Ser Val Val Thr Val Pro Ser Ser Ser Leu Gly Thr Gln Thr
65                  70                 75                 80

Tyr Ile Cys Asn Val Asn His Lys Pro Ser Asn Thr Lys Val Asp Lys
                 85                 90                 95

Lys Val Glu Pro Lys Ser Cys Asp Lys Thr His Thr Cys Pro Pro Cys
                100                105                110

Pro Ala Pro Glu Leu Leu Gly Gly Pro Ser Val Phe Leu Phe Pro Pro
             115                120                125

Lys Pro Lys Asp Thr Leu Met Ile Ser Arg Thr Pro Glu Val Thr Cys
         130                135                140

Val Val Val Asp Val Ser His Glu Asp Pro Glu Val Lys Phe Asn Trp
145                 150                155                160

Tyr Val Asp Gly Val Glu Val His Asn Ala Lys Thr Lys Pro Arg Glu
                165                170                175

Glu Gln Tyr Asn Ser Thr Tyr Arg Val Val Ser Val Leu Thr Val Leu
             180                185                190

His Gln Asp Trp Leu Asn Gly Lys Glu Tyr Lys Cys Lys Val Ser Asn
         195                200                205

Lys Ala Leu Pro Ala Pro Ile Glu Lys Thr Ile Ser Lys Ala Lys Gly
         210                215                220

Gln Pro Arg Glu Pro Gln Val Tyr Thr Leu Pro Pro Ser Arg Asp Glu
225                 230                235                240

Leu Thr Lys Asn Gln Val Ser Leu Thr Cys Leu Val Lys Gly Phe Tyr
                245                250                255

Pro Ser Asp Ile Ala Val Glu Trp Glu Ser Asn Gly Gln Pro Glu Asn
```

```
                260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 27
<211> LENGTH: 328
<212> TYPE: PRT
<213> ORGANISM: Artificial sequence
<220> FEATURE:
<223> OTHER INFORMATION: DA303v2

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Pro Pro Ser
            100                 105                 110

Pro Ala Pro Glu Tyr Gln Trp Gly Pro Met Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Lys Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Asp Leu Thr Val Asp Lys Ser Arg Trp Gln Gln Gly Asn
```

```
            290                 295                 300
Val Phe Ser Cys Ser Val Met His Glu Ala Leu His Asn His Tyr Thr
305                 310                 315                 320

Gln Lys Ser Leu Ser Leu Ser Pro
            325
```

<210> SEQ ID NO 28
<211> LENGTH: 328
<212> TYPE: PRT
<213> ORGANISM: Artificial sequence
<220> FEATURE:
<223> OTHER INFORMATION: DB220v2

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Ser Pro Pro Ser
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Asp Ala Leu Pro Met Pro Ile Glu Glu Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Asp Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
```

<210> SEQ ID NO 29
<211> LENGTH: 328
<212> TYPE: PRT
<213> ORGANISM: Artificial sequence
<220> FEATURE:
<223> OTHER INFORMATION: Kn125

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Gln Trp Gly Pro Met Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ala Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Cys Thr Leu Pro Pro Ser Arg Asp Glu
225                 230                 235                 240

Leu Thr Lys Asn Gln Val Ser Leu Trp Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 30
<211> LENGTH: 328
<212> TYPE: PRT

<213> ORGANISM: Artificial sequence
<220> FEATURE:
<223> OTHER INFORMATION: H1076

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Glu Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Asp Ala Leu Pro Met Pro Ile Glu Glu Thr Ile Ser Lys Ala Lys Gly
    210                 215                 220

Gln Pro Arg Glu Pro Gln Val Tyr Thr Leu Pro Pro Ser Arg Cys Glu
225                 230                 235                 240

Leu Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 31
<211> LENGTH: 328
<212> TYPE: PRT
<213> ORGANISM: Artificial sequence
<220> FEATURE:
<223> OTHER INFORMATION: F760

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 32
<211> LENGTH: 330
<212> TYPE: PRT
<213> ORGANISM: Artificial sequence
<220> FEATURE:
<223> OTHER INFORMATION: mFa55

<400> SEQUENCE: 32

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30
```

```
Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
 50                  55                  60

Ser Ser Ser Val Thr Val Thr Ser Ser Thr Trp Pro Ser Gln Ser Ile
 65                  70                  75                  80

Thr Cys Asn Val Ala His Pro Ala Ser Ser Thr Lys Val Asp Lys Lys
                 85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Asp Val Phe Ile Phe Pro Pro
            115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
            210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 33
<211> LENGTH: 328
<212> TYPE: PRT
<213> ORGANISM: Artificial sequence
<220> FEATURE:
<223> OTHER INFORMATION: F760nN17

<400> SEQUENCE: 33

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Arg Gly Gly Pro Lys Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro
            325

<210> SEQ ID NO 34
<211> LENGTH: 107
<212> TYPE: PRT
<213> ORGANISM: Mus musculus

<400> SEQUENCE: 34

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
            85                  90                  95

Pro Ile Val Lys Ser Phe Asn Arg Asn Glu Cys
            100                 105

<210> SEQ ID NO 35
<211> LENGTH: 447
<212> TYPE: PRT
<213> ORGANISM: Artificial sequence
<220> FEATURE:
<223> OTHER INFORMATION: MRAH-DA303v2.n.n

<400> SEQUENCE: 35

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 36
<211> LENGTH: 447
<212> TYPE: PRT
<213> ORGANISM: Artificial sequence
<220> FEATURE:
<223> OTHER INFORMATION: MRAH-DA303v2.n.HATF.B

<400> SEQUENCE: 36

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Ser Pro Pro Ser Pro Ala Pro Glu Tyr Gln Trp Gly Pro
225                 230                 235                 240

Met Val Phe Leu Phe Pro Pro Lys Pro Lys Asp Thr Leu Met Ile Ser
                245                 250                 255

Arg Thr Pro Glu Val Thr Cys Val Val Val Asp Val Ser Asp Glu Glu
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ala Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Thr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Phe Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
    435                 440                 445

<210> SEQ ID NO 37
<211> LENGTH: 447
<212> TYPE: PRT
<213> ORGANISM: Artificial sequence
<220> FEATURE:
<223> OTHER INFORMATION: MRAH-DB220v2.n.n

<400> SEQUENCE: 37

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Ser Pro Ser Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Asp Val Ser His Glu Glu
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Leu Pro Met Pro Ile Glu Glu
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Tyr Leu
385                 390                 395                 400

Asp Ser Asp Gly Ser Phe Phe Leu Tyr Ser Asp Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 38
<211> LENGTH: 447
<212> TYPE: PRT
<213> ORGANISM: Artificial sequence
<220> FEATURE:
<223> OTHER INFORMATION: MRAH-DB220v2.n.HATF.A

<400> SEQUENCE: 38

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
                165             170             175

Gln Ser Ser Gly Leu Tyr Ser Leu Ser Ser Val Val Thr Val Pro Ser
            180             185             190

Ser Ser Leu Gly Thr Gln Thr Tyr Ile Cys Asn Val Asn His Lys Pro
        195             200             205

Ser Asn Thr Lys Val Asp Lys Lys Val Glu Pro Lys Ser Cys Asp Lys
    210             215             220

Thr His Thr Ser Pro Pro Ser Pro Ala Pro Glu Leu Leu Gly Gly Pro
225             230             235             240

Ser Val Phe Leu Phe Pro Pro Lys Pro Lys Asp Thr Leu Met Ile Ser
                245             250             255

Arg Thr Pro Glu Val Thr Cys Val Val Val Asp Val Ser His Glu Glu
            260             265             270

Pro Glu Val Lys Phe Asn Trp Tyr Val Asp Gly Val Glu Val His Asn
        275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Lys Val Ser Asn Asp Ala Leu Pro Met Pro Ile Glu Glu
                325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val His Leu Thr
        355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Tyr Leu
385             390             395             400

Asp Ser Asp Gly Ser Phe Ala Leu Tyr Ser Asp Leu Thr Val Asp Lys
                405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro
    435             440             445
```